United States Patent
Makinoshima et al.

(10) Patent No.: US 10,294,183 B2
(45) Date of Patent: *May 21, 2019

(54) COMPOUND, RESIN, MATERIAL FOR FORMING UNDERLAYER FILM FOR LITHOGRAPHY, UNDERLAYER FILM FOR LITHOGRAPHY, PATTERN FORMING METHOD, AND METHOD FOR PURIFYING THE COMPOUND OR RESIN

(71) Applicant: Mitsubishi Gas Chemical Company, Inc., Tokyo (JP)

(72) Inventors: Takashi Makinoshima, Kanagawa (JP); Masatoshi Echigo, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/125,503

(22) PCT Filed: Mar. 13, 2015

(86) PCT No.: PCT/JP2015/057471
§ 371 (c)(1),
(2) Date: Sep. 12, 2016

(87) PCT Pub. No.: WO2015/137486
PCT Pub. Date: Sep. 17, 2015

(65) Prior Publication Data
US 2017/0073288 A1    Mar. 16, 2017

(30) Foreign Application Priority Data
Mar. 13, 2014 (JP) ................ 2014-050768

(51) Int. Cl.
| | |
|---|---|
| G03F 7/11 | (2006.01) |
| C07C 39/15 | (2006.01) |
| C08G 8/04 | (2006.01) |
| C09D 161/06 | (2006.01) |
| C07C 37/68 | (2006.01) |
| C08G 8/10 | (2006.01) |
| C09D 161/12 | (2006.01) |
| G03F 7/16 | (2006.01) |
| G03F 7/20 | (2006.01) |
| G03F 7/32 | (2006.01) |

(52) U.S. Cl.
CPC ............ *C07C 39/15* (2013.01); *C07C 37/68* (2013.01); *C08G 8/04* (2013.01); *C08G 8/10* (2013.01); *C09D 161/06* (2013.01); *C09D 161/12* (2013.01); *G03F 7/11* (2013.01); *G03F 7/16* (2013.01); *G03F 7/20* (2013.01); *G03F 7/327* (2013.01)

(58) Field of Classification Search
CPC ......... C07C 39/15; C07C 37/68; G03F 7/327; G03F 7/20; G03F 7/16; G03F 7/11; C09D 161/12
See application file for complete search history.

(56) References Cited

U.S. PATENT DOCUMENTS

| | | | |
|---|---|---|---|
| 3,702,245 A | 11/1972 | Simon et al. | |
| 4,115,128 A | 9/1978 | Kita | |
| 4,670,495 A * | 6/1987 | Evans | ............... C07C 39/15 |
| | | | 252/406 |
| 5,173,389 A | 12/1992 | Uenishi | |
| 5,281,689 A * | 1/1994 | Bendler | ............... C07C 37/055 |
| | | | 528/196 |
| 5,565,300 A | 10/1996 | Uenishi | |
| 9,372,404 B2 | 6/2016 | Watanabe et al. | |
| 2002/0156189 A1 | 10/2002 | Ogura | |
| 2004/0254327 A1* | 12/2004 | Boyles | ............... C07C 17/093 |
| | | | 528/86 |

(Continued)

FOREIGN PATENT DOCUMENTS

| | | |
|---|---|---|
| CN | 101889247 A | 11/2010 |
| CN | 103304385 A | 9/2013 |

(Continued)

OTHER PUBLICATIONS

Boyles et al ,"Synthesis of High Aspect Ratio Bisphenols and Polycarbonates Incorporating Bisaryl Units", Macromolecules, 2005, 38 (9), pp. 3622-3629, DOI: 10.1021/ma048616m Publication Date (Web): Mar. 30, 2005.*
Cammack et al . (2006). Oxford Dictionary of Biochemistry and Molecular Biology(2nd Edition). Oxford University Press. pp. 419, 422 Onlie Version available at hhtps://app.knovel.com.*
"Methine group:", Illustrated Glossary of Organic Chemistry—Methylene group, 2 pages Copyright 2010-2017 Steven A. Hardinger, Department of Chemistry & Biochemistry, UCLA. All rights reserved. 2 pages downloaded Feb. 16, 2018.*
9 Organic Chemistry Nomenclature Conventions to Know—Master Organic Chemistry by James, 26 pages cpoyright 2018 MasterOrganic Chemstry.com down loaged Feb. 15, 2018.*

(Continued)

*Primary Examiner* — Cynthia Hamilton
(74) *Attorney, Agent, or Firm* — Fitch, Even, Tabin & Flannery LLP

(57) ABSTRACT

The compound according to the present invention is represented by a specific formula. The compound according to the present invention has a structure according to the specific formula, and therefore can be applied to a wet process and is excellent in heat resistance and etching resistance. In addition, the compound according to the present invention has such a specific structure, and therefore has a high heat resistance, a relatively high carbon concentration, a relatively low oxygen concentration and also a high solvent solubility. Therefore, the compound according to the present invention can be used to form an underlayer film whose degradation is suppressed at high-temperature baking and which is also excellent in etching resistance to oxygen plasma etching or the like. Furthermore, the compound is also excellent in adhesiveness with a resist layer and therefore can form an excellent resist pattern.

25 Claims, No Drawings

(56) References Cited

U.S. PATENT DOCUMENTS

| | | |
|---|---|---|
| 2005/0255712 A1 | 11/2005 | Kato et al. |
| 2007/0059632 A1 | 3/2007 | Oguro |
| 2008/0044757 A1 | 2/2008 | De Silva et al. |
| 2008/0113294 A1 | 5/2008 | Echigo |
| 2008/0153031 A1 | 6/2008 | Echigo et al. |
| 2009/0081582 A1 | 3/2009 | Hattori |
| 2010/0316950 A1 | 12/2010 | Oguro et al. |
| 2011/0177459 A1 | 7/2011 | Ogihara et al. |
| 2012/0064725 A1 | 3/2012 | Kinsho et al. |
| 2012/0171611 A1 | 7/2012 | Ideno et al. |
| 2013/0302990 A1 | 11/2013 | Watanabe et al. |
| 2014/0065533 A1 | 3/2014 | Wu et al. |
| 2014/0186776 A1 | 7/2014 | Uchiyama |
| 2014/0224765 A1 | 8/2014 | Minegishi |
| 2014/0248561 A1 | 9/2014 | Echigo |
| 2014/0308615 A1 | 10/2014 | Echigo |
| 2014/0349222 A1 | 11/2014 | Satoshi |
| 2015/0037735 A1 | 2/2015 | Yang et al. |
| 2015/0212418 A1* | 7/2015 | Nishimaki ............ C08G 8/04 438/703 |
| 2016/0068709 A1* | 3/2016 | Endo ............... C09D 179/04 438/703 |
| 2017/0073288 A1 | 3/2017 | Makinoshima et al. |
| 2017/0075220 A1* | 3/2017 | Sato .................. C07C 39/15 |
| 2017/0349564 A1 | 12/2017 | Toida |
| 2018/0029968 A1* | 2/2018 | Toida ................ C07C 43/275 |
| 2018/0044270 A1 | 2/2018 | Horiuchi |
| 2018/0081270 A1 | 3/2018 | Echigo |
| 2018/0107113 A1 | 4/2018 | Toida |

FOREIGN PATENT DOCUMENTS

| | | |
|---|---|---|
| CN | 103804196 A | 5/2014 |
| CN | 104557552 A | 4/2015 |
| DE | 1167854 B | 4/1964 |
| EP | 0 395 049 A1 * | 10/1990 |
| EP | 0395049 A1 | 10/1990 |
| EP | 0 440 238 A2 * | 8/1991 |
| EP | 0440238 A2 | 8/1991 |
| EP | 0604056 A2 | 6/1994 |
| EP | 2660257 A1 | 11/2013 |
| EP | 2 743 770 A1 | 6/2014 |
| EP | 3118183 A1 | 1/2017 |
| EP | 3118684 A1 | 1/2017 |
| JP | S54-037492 B1 | 11/1979 |
| JP | H02-285351 A | 11/1990 |
| JP | H03-228051 A | 10/1991 |
| JP | 04297430 A | 10/1992 |
| JP | 05019463 A | 1/1993 |
| JP | H05-067701 A | 3/1993 |
| JP | 06242601 A | 9/1994 |
| JP | H07-211031 A | 10/1995 |
| JP | H08-137100 A | 5/1996 |
| JP | 09106070 A | 4/1997 |
| JP | H10-161332 A | 6/1998 |
| JP | H10-307384 A | 11/1998 |
| JP | 2001-122828 A | 5/2001 |
| JP | 2002275112 A | 9/2002 |
| JP | 2002-334869 A | 11/2002 |
| JP | 2004-177668 A | 6/2004 |
| JP | 2004-271838 A | 9/2004 |
| JP | 2005-187335 A | 7/2005 |
| JP | 2005-250434 A | 9/2005 |
| JP | 2005266741 A | 9/2005 |
| JP | 2005-326838 A | 11/2005 |
| JP | 2006259482 A | 9/2006 |
| JP | 2006-276742 A | 10/2006 |
| JP | 2007-204574 A | 8/2007 |
| JP | 2007-226170 A | 9/2007 |
| JP | 2007-226204 A | 9/2007 |
| JP | 2007-241271 A | 9/2007 |
| JP | 2008-145539 A | 6/2008 |
| JP | 2009080203 A | 4/2009 |
| JP | 2009-173623 A | 8/2009 |
| JP | 2010077038 A | 4/2010 |
| JP | 2012-077295 A | 4/2012 |
| JP | 2012083731 A | 4/2012 |
| SG | 11201607443 | 10/2016 |
| SG | 11201607444V A | 10/2016 |
| WO | 2004037879 A2 | 5/2004 |
| WO | 2004/066377 A1 | 8/2004 |
| WO | 2005101127 A1 | 10/2005 |
| WO | 2009/072465 A1 | 6/2009 |
| WO | 2011/034062 A1 | 3/2011 |
| WO | 2012153991 A2 | 11/2012 |
| WO | 2012165507 A1 | 12/2012 |
| WO | 2013024777 A1 | 2/2013 |
| WO | 2013/036546 A2 | 3/2013 |
| WO | 2013/134997 A1 | 9/2013 |
| WO | WO 2014/024836 A1 * | 2/2014 |
| WO | 2015/137486 A1 | 9/2015 |
| WO | 2015137485 A1 | 9/2015 |
| WO | 2016/129679 A1 | 8/2016 |
| WO | 2016/158456 A1 | 10/2016 |
| WO | 2016/163456 A1 | 10/2016 |
| WO | 2017/038979 A1 | 3/2017 |
| WO | 2017/043561 A1 | 3/2017 |

OTHER PUBLICATIONS

T. Nakayama, M. Nomura, K. Haga, M. Ueda: Bull. Chem. Soc. Jpn., 71,1979(1998).

De Silva, Anuja; Forman, Drew; Ober, Christopher K., Molecular glass resists for EUV lithography, Proceedings of SPIE—The International Society for Optical Engineering (Pt. 2, Advances in Resist Technology and Processing XXIII), 2006, 6153, 615341/1-615341/10.

Sundberg, Linda K.; Wallraff, Gregory M.; Friz, Alexander M.; Davis, Blake W.; Swanson, Sally A.; Brock, Phillip J.; Rettner, Charles T.; Hinsberg, William D., Visualization of the develop process, Proceedings of SPIE (Advances in Resist Materials and Processing Technology XXVIII), 2011, 7972, 797201/1-797201/10.

Arai, Tadashi; Hattori, Takashi; Shiraishi, Hiroshi; Fukuda, Hiroshi, Polyphenol-based positive-tone EB resist: Resist shade mask, Journal of Photopolymer Science and Technology, 2004, 17(4), 567-573.

Schultz, Andreas et al., Tetraphenylethene-derived columnar liquid crystals and their oxidative photocyclization, European Journal of Organic Chemistry, 2003, (15), p. 2829-2839, p. 2832, scheme 4, compound 17.

Reddy, D. Shekhar et al., Charge-transfer diamondoid lattices: an unprecedentedly huge and highly catenating diamondoid network arising from a tetraphenol as a tetrahedral node and benzoquinone as a linear spacer, Angewandte Chemie, International Edition, 2000, 39(23), p. 4266-4268, scheme 1, compound 1.

Vogl, Erasmus M. et al., Linking BINOL: C2-symmetric ligands for investigations on asymmetric catalysis, Tetrahedron Letters, 1998, 39(43), p. 7917-7920, pp. 7918 to 7919, compounds 2, 9.

Ihori, Yoichi, et al., "Chiral Zirconium Catalysts Using Multidentate BINOL Derivatives for Catalytic Enantioselective Mannich-Type Reactions; Ligand Optimization and Approaches to Elucidation of the Catalyst Structure," Journal of the American Chemical Society, 2005, vol. 127, No. 44, pp. 15528-15535.

Amaya, Toru, Miyasaka, Akihiro, and Hirao, Toshikazu, "Synthesis of three-dimensionally arranged bis-biphenol ligand on hexaarylbenzene scaffold and its application for cross-pinacol coupling reaction," Tetrahedron Letters, Jul. 2, 2011, vol. 52, pp. 4567-4569.

Cantin, Katy, et al. "Studies Toward the Synthesis of Phenylacetylene Macrocycle Based Rotaxane Precursors as Building Blocks for Organic Nanotubes," European Journal of Organic Chemistry, 2012, pp. 5335-5349.

Chaumont, Clement, et al., "Synthesis, topology and energy analysis of crystaline resorcinol-based oligophenylene molecules with various symmetries," CrystEngComm, vol. 15, No. 34, Jan. 2013, pp. 6845-6862.

Chen, Huanqing, et al., "Biphen[n]arenes," Chemical Science; vol. 6, No. 197; The Royal Society of Chemistry; 2015; pp. 197-202.

(56) References Cited

OTHER PUBLICATIONS

Ghebremariam, Bereket, and Matile, Stefan, "Synthesis of Asymmetric Septi-(p-Phenylene)s," Tetrahedron Letters, May 13, 1998, vol. 39, pp. 5335-5338.

Jang, Cheong-Jin, Ryu, Ja-Hyoung, Lee, Joon-Dong, Sohn, Deawon, and Lee Myongsoo, "Synthesis and Supramolecular Nanostructure of Amphiphilic Rigid Aromatic-Flexible Dendritic Block Molecules," Chemistry of Materials, Sep. 10, 2004, vol. 16, pp. 4226-4231.

Lin, Ying, et al., "Palladium-Catalyzed [3+2] Cycloaddition Reaction of (Diarylmethylene)-cyclopropa[b]naphthalenes with Arynes: An Efficient Synthesis of 11-(Diarylmethylene)-11H-benzo[b]fluorenes," European Journal of Organic Chemistry, vol. 2011, No. 16, Jan. 2011, pp. 2993-3000.

Pegenau, Annegret, et al., "The Importance of Micro Segregation for Mesophase Formation: Thermotropic Columnar Mesophases of Tetrahedral and other Low-Aspect-Ratio Organic Materials," Chem. Eur. J., vol. 5, No. 5, May 1999, pp. 1643-1660.

Rathore, Rajendra, Burns, Carrie L., and Deselnicu, Mihaela I., "Multiple-Electron Transfer in a Single Step. Design and Synthesis of Highly Charged Cation-Radical Salts," Organic Letters, Sep. 1, 2001, vol. 3, No. 18, pp. 2887-2890.

Ryu, Ja-Hyoung, et al.," Self-Assembling Molecular Dumbbells: From Nanohelices to Nanocapsules Triggered by Guest Intercalation," Angewandte Chemie International Edition, vol. 45, No. 32, 2006, pp. 5304-5307.

Yamada, Arisa, et al.; Development of High Resolution Molecular Resist Based on Tris((hydroxypheny)pheny)benzene; Journal of Photopolymer Science and Technology; vol. 23, No. 1; 2010; pp. 91-95.

Mora et al., "Interface Engineering of Synthetic Pores: Towards Hypersensitive Biosensors," Chemistry—A European Journal, 2008, vol.14, pp. 1947-1953.

\* cited by examiner

COMPOUND, RESIN, MATERIAL FOR FORMING UNDERLAYER FILM FOR LITHOGRAPHY, UNDERLAYER FILM FOR LITHOGRAPHY, PATTERN FORMING METHOD, AND METHOD FOR PURIFYING THE COMPOUND OR RESIN

CROSS-REFERENCE TO RELATED APPLICATIONS

This application is a U.S. national phase application filed under 35 U.S.C. § 371 of International Application PCT/JP2015/057471, filed on Mar. 13, 2015, designating the United States, which claims priority from Japanese Application Number 2014-050768, filed Mar. 13, 2014.

TECHNICAL FIELD

The present invention relates to a compound or a resin having a specific structure. It also relates to a material for forming an underlayer film for lithography, containing the compound or the resin, an underlayer film for lithography, obtained from the material, and a pattern forming method using the material. Furthermore, it relates to a method for purifying the compound or the resin.

BACKGROUND ART

Semiconductor devices are manufactured through microfabrication by lithography using a photoresist material, but are required to be made finer by a pattern rule in accordance with the increase in integration degree and the increase in speed of LSI in recent years. In lithography using exposure to light, which is currently used as a general-purpose technique, the resolution is now approaching the intrinsic limitation associated with the wavelength of the light source.

A light source for lithography, for use in forming a resist pattern, has a shorter wavelength from a KrF excimer laser (248 nm) to an ArF excimer laser (193 nm). However, as the resist pattern is made finer and finer, there arise a problem of resolution and a problem of collapse of the resist pattern after development, and therefore there is demanded for making a resist film thinner. If the resist film is merely made thinner in response to such a demand, it is difficult to achieve the resist pattern having a film thickness sufficient for processing a substrate. Accordingly, there is increasingly required a process in which not only the resist pattern but also a resist underlayer film is prepared between a resist and a semiconductor substrate to be processed and the resist underlayer film is allowed to have a function as a mask at the time of processing the substrate.

Currently, as the resist underlayer film for such a process, various ones are known. Examples can include a resist underlayer film for lithography, having a selection ratio of dry etching rate close to the resist, unlike a conventional resist underlayer film having a high etching rate. As the material for forming such a resist underlayer film for lithography, there has been proposed a material for forming an underlayer film for multilayer resist process, containing a resin component having at least a substituent which releases a terminal group to form a sulfonic acid residue when a predetermined energy is applied, and a solvent (see, for example, Patent Literature 1). In addition, examples can also include a resist underlayer film for lithography, having a smaller selection ratio of dry etching rate than the resist. As the material for forming such a resist underlayer film for lithography, there has been proposed a resist underlayer film material including a polymer having a specific repeating unit (see, for example, Patent Literature 2). Furthermore, examples can include a resist underlayer film for lithography, having a smaller selection ratio of dry etching rate than the semiconductor substrate. As the material for forming such a resist underlayer film for lithography, there has been proposed a resist underlayer film material including a polymer formed by co-polymerizing a repeating unit of acenaphthylene, and a substituted or non-substituted repeating unit having a hydroxy group (see, for example, Patent Literature 3).

On the other hand, as a material for allowing such a resist underlayer film to have a high etching resistance, an amorphous carbon underlayer film is well known, which is formed by CVD using methane gas, ethane gas, acetylene gas, or the like as a raw material. However, there is demanded, in terms of process, a resist underlayer film material that can form a resist underlayer film in a wet process such as a spin coating method or screen printing.

In addition, as a material that is excellent in optical characteristics and etching resistance and that is capable of being dissolved in a solvent and being applied to a wet process, the present inventors have proposed a composition for forming an underlayer film for lithography, which contains a naphthalene formaldehyde polymer including a specific constituent unit, and an organic solvent (see, for example, Patent Literatures 4 and 5).

Meanwhile, with respect to a forming method of an intermediate layer for use in forming a resist underlayer film in a three-layer process, for example, known are a forming method of a silicon nitride film (see, for example, Patent Literature 6), and a CVD forming method of a silicon nitride film (see, for example, Patent Literature 7). In addition, as an intermediate layer material for a three-layer process, known is a material containing a silsesquioxane-based silicon compound (see, for example, Patent Literatures 8 and 9).

CITATION LIST

Patent Literature

Patent Literature 1: Japanese Patent Laid-Open No. 2004-177668
Patent Literature 2: Japanese Patent Laid-Open No. 2004-271838
Patent Literature 3: Japanese Patent Laid-Open No. 2005-250434
Patent Literature 4: International Publication No. WO 2009/072465
Patent Literature 5: International Publication No. WO 2011/034062
Patent Literature 6: Japanese Patent Laid-Open No. 2002-334869
Patent Literature 7: International Publication No. WO 2004/066377
Patent Literature 8: Japanese Patent Laid-Open No. 2007-226170
Patent Literature 9: Japanese Patent Laid-Open No. 2007-226204

SUMMARY OF INVENTION

As described above, many materials for forming an underlayer film for lithography have been conventionally proposed, but there are no ones that not only have such a high solvent solubility as to be able to be applied to a wet process such as a spin coating method or screen printing, but also simultaneously satisfy heat resistance and etching resistance at a high level, and thus a new material is required to be developed.

The present invention has been made in view of the above problem, and an object thereof is to provide a compound, a resin, a material for forming an underlayer film for lithography, and an underlayer film for lithography, which can be applied to a wet process in formation of a photoresist underlayer film and which are excellent in heat resistance and etching resistance. Another object of the present invention is to provide a pattern forming method, and a method for purifying the compound or the resin.

The present inventors have intensively studied to solve the above problem, and as a result, have found that the above problem can be solved by using a compound or a resin having a specific structure, thereby leading to the completion of the present invention.

That is, the present invention is as follows.

[1]

A compound represented by the following formula (1):

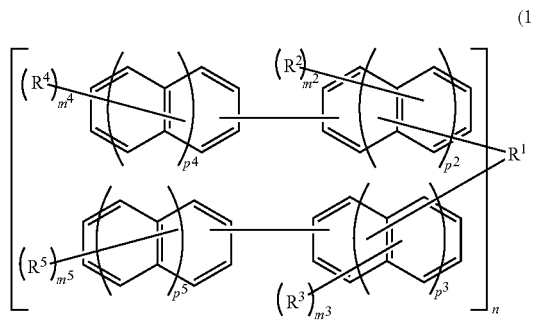

(1)

wherein $R^1$ is a 2n-valent group having 1 to 30 carbon atoms, each of $R^2$ to $R^5$ is independently a linear, branched or cyclic alkyl group having 1 to 10 carbon atoms, an aryl group having 6 to 10 carbon atoms, an alkenyl group having 2 to 10 carbon atoms, a thiol group or a hydroxyl group, wherein at least one $R^4$ and/or at least one $R^5$ is a hydroxyl group and/or a thiol group, each of $m^2$ and $m^3$ is independently an integer of 0 to 8, each of $m^4$ and $m^5$ is independently an integer of 0 to 9, wherein at least one of $m^4$ and $m^5$ is an integer of 1 to 9, n is an integer of 1 to 4, and each of $p^2$ to $p^5$ is independently an integer of 0 to 2.

[2]

The compound according to [1], wherein at least one $R^2$ and/or at least one $R^3$ is a hydroxyl group and/or a thiol group.

[3]

The compound according to [1] or [2], wherein the compound represented by the formula (1) is a compound represented by the following formula (1a):

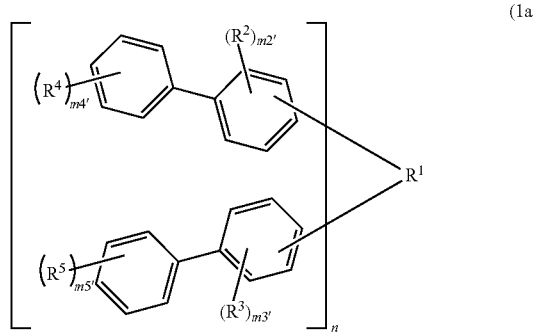

(1a)

wherein $R^1$ to $R^5$ and n are the same as defined in the formula (1), each of $m^{2'}$ and $m^{3'}$ is independently an integer of 0 to 4, and each of $m^{4'}$ and $m^{5'}$ is independently an integer of 0 to 5, wherein at least one of $m^{4'}$ and $m^{5'}$ is an integer of 1 to 5.

[4]

The compound according to any of [1] to [3], wherein n is 1 and $R^1$ is a group represented by $R^A$—$R^B$, wherein $R^A$ is a methine group and $R^B$ is an aryl group having 7 or more carbon atoms.

[5]

The compound according to [3], wherein the compound represented by the formula (1a) is a compound represented by the following formula (1b):

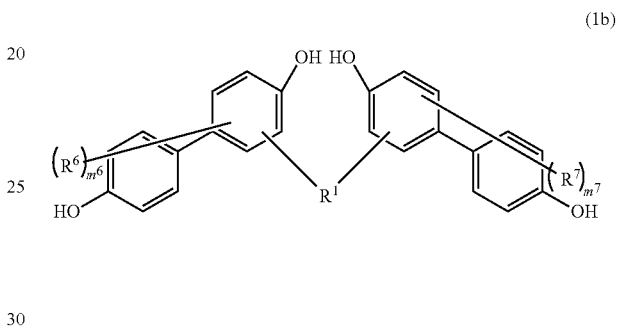

(1b)

wherein $R^1$ is the same as defined in the formula (1), each of $R^6$ and $R^7$ is independently a linear, branched or cyclic alkyl group having 1 to 10 carbon atoms, an aryl group having 6 to 10 carbon atoms, an alkenyl group having 2 to 10 carbon atoms, a thiol group or a hydroxyl group, and each of $m^6$ and $m^7$ is independently an integer of 0 to 7.

[6]

The compound according to [5], wherein the compound represented by the formula (1b) is represented by the following formula (BiF-1).

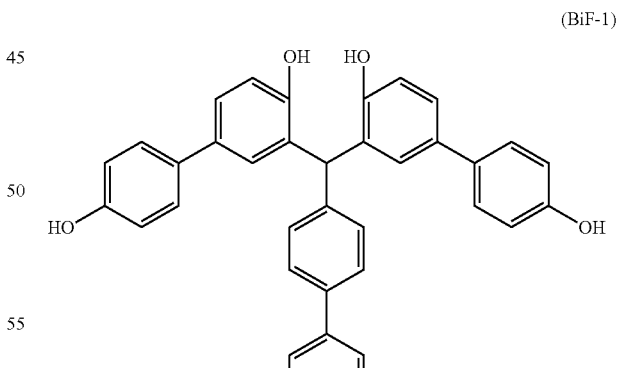

(BiF-1)

[7]

A resin obtained by using the compound according to any of [1] to [6] as a monomer.

[8]

A resin having the following structure represented by formula (2):

(2)

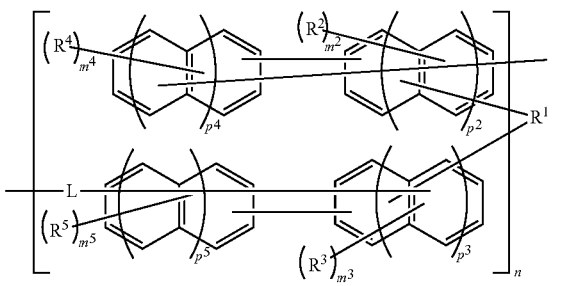

wherein $R^1$ is a 2n-valent group having 1 to 30 carbon atoms, each of $R^2$ to $R^5$ is independently a linear, branched or cyclic alkyl group having 1 to 10 carbon atoms, an aryl group having 6 to 10 carbon atoms, an alkenyl group having 2 to 10 carbon atoms, a thiol group or a hydroxyl group, wherein at least one $R^4$ and/or at least one $R^5$ is a hydroxyl group and/or a thiol group, L represents a single bond, or a linear or branched alkylene group having 1 to 20 carbon atoms, each of $m^2$ and $m^3$ is independently an integer of 0 to 8, each of $m^4$ and $m^5$ is independently an integer of 0 to 9, wherein at least one of $m^4$ and $m^5$ is an integer of 1 to 9, n is an integer of 1 to 4, and each of $p^2$ to $p^5$ is independently an integer of 0 to 2.

[9]
A material for forming an underlayer film for lithography, comprising the compound according to any of [1] to [6].

[10]
A material for forming an underlayer film for lithography, comprising the resin according to [7] or [8].

[11]
The material for forming the underlayer film for lithography according to [9] or [10], further comprising an organic solvent.

[12]
The material for forming the underlayer film for lithography according to any of [9] to [11], further comprising an acid generator.

[13]
The material for forming the underlayer film for lithography according to any of [9] to [12], further comprising a crosslinking agent.

[14]
An underlayer film for lithography, formed from the material for forming the underlayer film for lithography according to any of [9] to [13].

[15]
A resist pattern forming method, comprising
step (A-1) of forming an underlayer film on a substrate by using the material for forming the underlayer film according to any of [9] to [13],
step (A-2) of forming at least one photoresist layer on the underlayer film, and
step (A-3) of, after step (A-2), irradiating a predetermined region of the photoresist layer with radiation, followed by developing with an alkali.

[16]
A circuit pattern forming method comprising
step (B-1) of forming an underlayer film on a substrate by using the material for forming the underlayer film according to any of [9] to [13],
step (B-2) of forming an intermediate layer film on the underlayer film by using a silicon atom-containing resist intermediate layer film material,
step (B-3) of forming at least one photoresist layer on the intermediate layer film,
step (B-4) of, after step (B-3), irradiating a predetermined region of the photoresist layer with radiation, followed by developing with an alkali to form a resist pattern, and
step (B-5) of, after step (B-4), etching the intermediate layer film with the resist pattern as a mask, etching the underlayer film with an obtained intermediate layer film pattern as an etching mask and etching the substrate with an obtained underlayer film pattern as an etching mask, to form a pattern on the substrate.

[17]
A method for purifying the compound according to any of [1] to [6], or the resin according to claim 7 or 8, the method comprising
a step of bringing a solution comprising an organic solvent optionally immiscible with water, and the compound or the resin into contact with an acidic aqueous solution for extraction.

[18]
The method according to [17], wherein the acidic aqueous solution is an aqueous solution of at least one mineral acid selected from the group consisting of hydrochloric acid, sulfuric acid, nitric acid and phosphoric acid, or an aqueous solution of at least one organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid.

[19]
The method according to [17] or [18], wherein the organic solvent optionally immiscible with water is toluene, 2-heptanone, cyclohexanone, cyclopentanone, methyl isobutyl ketone, propylene glycol monomethyl ether acetate or ethyl acetate.

[20]
The method according to any of [17] to [19], further comprising a step of performing an extraction treatment with water, after the step of bringing the solution into contact with the acidic aqueous solution for extraction.

According to the present invention, it is possible to provide a material for forming an underlayer film for lithography, which can be applied to a wet process and which is useful for forming a photoresist underlayer film excellent in heat resistance and etching resistance.

DESCRIPTION OF EMBODIMENTS

Hereinafter, an embodiment (hereinafter, referred to as "the present embodiment") of the present invention will be described. It is to be noted that the present embodiments are illustrative for describing the present invention, and the present invention is not limited only to the present embodiments.

[Compound]
A compound of the present embodiment is represented by the following formula (1). The compound of the present embodiment has such a configuration, and therefore can be applied to a wet process in formation of a photoresist underlayer film and is excellent in heat resistance and etching resistance. In addition, the compound of the present embodiment has a specific structure, and therefore has a high heat resistance, a relatively high carbon concentration, a relatively low oxygen concentration and also a high solvent solubility. Therefore, the compound of the present embodiment can be used to thereby form an underlayer film whose degradation is suppressed at high-temperature baking and which is also excellent in etching resistance to oxygen plasma etching or the like. Furthermore, the compound is also excellent in adhesiveness with a resist layer and therefore can form an excellent resist pattern.

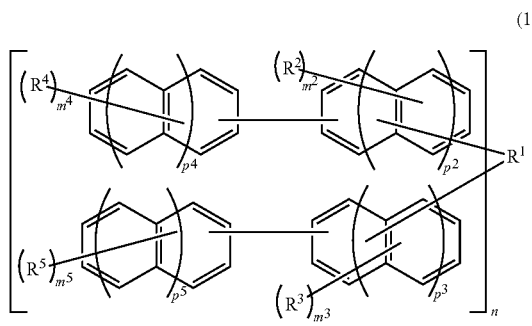
(1)

In the formula (1), $R^1$ is a 2n-valent group having 1 to 30 carbon atoms. The compound of the present embodiment has a structure in which respective aromatic rings are bonded with each other via $R^1$.

Each of $R^2$ to $R^5$ is independently a monovalent group selected from the group consisting of a linear, branched or cyclic alkyl group having 1 to 10 carbon atoms, an aryl group having 6 to 10 carbon atoms, an alkenyl group having 2 to 10 carbon atoms, a thiol group and a hydroxyl group, wherein at least one $R^4$ and/or at least one $R^5$ is a hydroxyl group and/or a thiol group.

Each of $m^2$ and $m^3$ is independently an integer of 0 to 8, and each of $m^4$ and $m^5$ is independently an integer of 0 to 9, wherein at least one of $m^4$ and $m^5$ is an integer of 1 to 9, namely, $m^4$ and $m^5$ are not 0 at the same time.

n is an integer of 1 to 4.

Each of $p^2$ to $p^5$ is independently an integer of 0 to 2.

Herein, the 2n-valent group means an alkylene group having 1 to 30 carbon atoms when n=1, an alkanetetrayl group having 1 to 30 carbon atoms when n=2, an alkanehexayl group having 2 to 30 carbon atoms when n=3, and an alkaneoctayl group having 3 to 30 carbon atoms when n=4. Examples of the 2n-valent group include those having a linear hydrocarbon group, a branched hydrocarbon group or a cyclic hydrocarbon group. Herein, the cyclic hydrocarbon group also includes a bridged cyclic hydrocarbon group. The 2n-valent group may also have an aromatic group having 6 to 30 carbon atoms.

The 2n-valent group may also have a double bond. The group may also have a hetero atom.

In the present embodiment, from the viewpoint of imparting availability of raw materials and heat resistance, it is preferable that n is 1 and $R^1$ is a group represented by $R^A$—$R^B$, wherein $R^A$ is a methine group and $R^B$ is an aryl group having 7 or more carbon atoms. Examples of the aryl group having 7 or more carbon atoms include, but not limited to the following, biphenyl, naphthalene, anthracene, pyrene, perylene, fluorene and triphenylmethane.

On the other hand, in the present embodiment, n is preferably an integer of 2 to 4 from the viewpoints of suppression of sublimation and an enhancement in heat resistance.

The compound represented by the formula (1) has a high heat resistance due to rigidity of its structure while having a relatively low molecular weight, and therefore it can be used even under a high-temperature baking condition. In addition, the compound has a relatively low molecular weight and a low viscosity, and therefore, even when being applied to a substrate having a step (in particular, fine space, hole pattern and the like), it can be easily filled uniformly in every part of the step. As a result, a material for forming an underlayer film for lithography using such a compound can be improved in terms of embedding properties in a relatively advantageous manner. In addition, the compound has a relatively high carbon concentration to thereby impart also a high etching resistance. Herein, the molecular weight of the compound of the present embodiment is preferably 5000 or less, more preferably 4000 or less, further preferably 3000 or less. Herein, the molecular weight can be measured by a method in Examples described later.

In the compound represented by the formula (1), at least one $R^2$ and/or at least one $R^3$ is preferably a hydroxyl group and/or a thiol group in terms of ease of crosslinking and solubility in an organic solvent.

The compound represented by the formula (1) is more preferably a compound represented by the following formula (1a) in terms of the supply of raw materials.

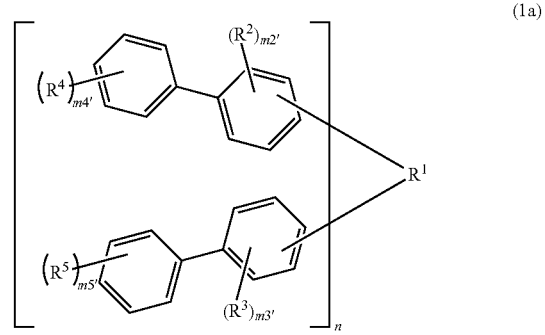
(1a)

In the formula (1a), $R^1$ to $R^5$ and n are the same as defined in the formula (1).

Each of $m^{2\prime}$ and $m^{3\prime}$ is independently an integer of 0 to 4, and each of $m^{4\prime}$ and $m^{5\prime}$ is independently an integer of 0 to 5, wherein at least one of $m^{4\prime}$ and $m^{5\prime}$ is an integer of 1 to 5, namely, $m^{4\prime}$ and $m^{5\prime}$ are not 0 at the same time.

The compound represented by the formula (1a) is further preferably a compound represented by the following formula (1b) in terms of solubility in an organic solvent.

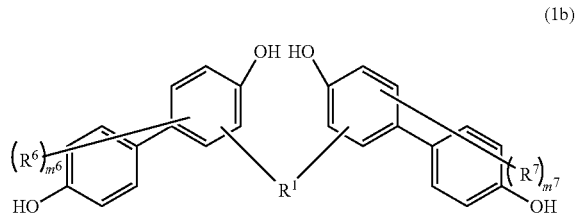
(1b)

In the formula (1b), $R^1$ is the same as defined in the formula (1).

Each of $R^6$ and $R^7$ is independently a linear, branched or cyclic alkyl group having 1 to 10 carbon atoms, an aryl group having 6 to 10 carbon atoms, an alkenyl group having 2 to 10 carbon atoms, a thiol group or a hydroxyl group.

Each of $m^6$ and $m^7$ is independently 0 to 7.

The compound represented by the formula (1b) is more further preferably a compound represented by the following formula (BiF-1) in terms of further solubility in an organic solvent.
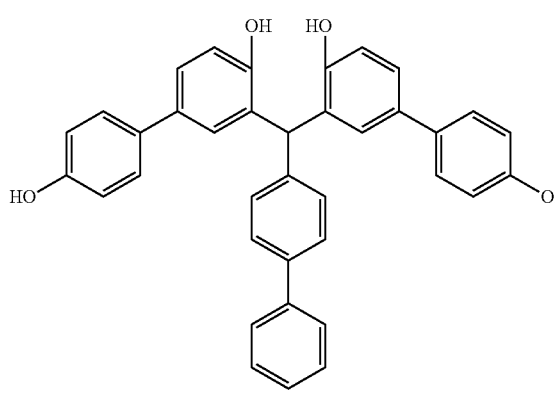
(BiF-1)
Hereinafter, specific examples of the compound represented by the formula (1) are shown, but are not limited to those described herein.
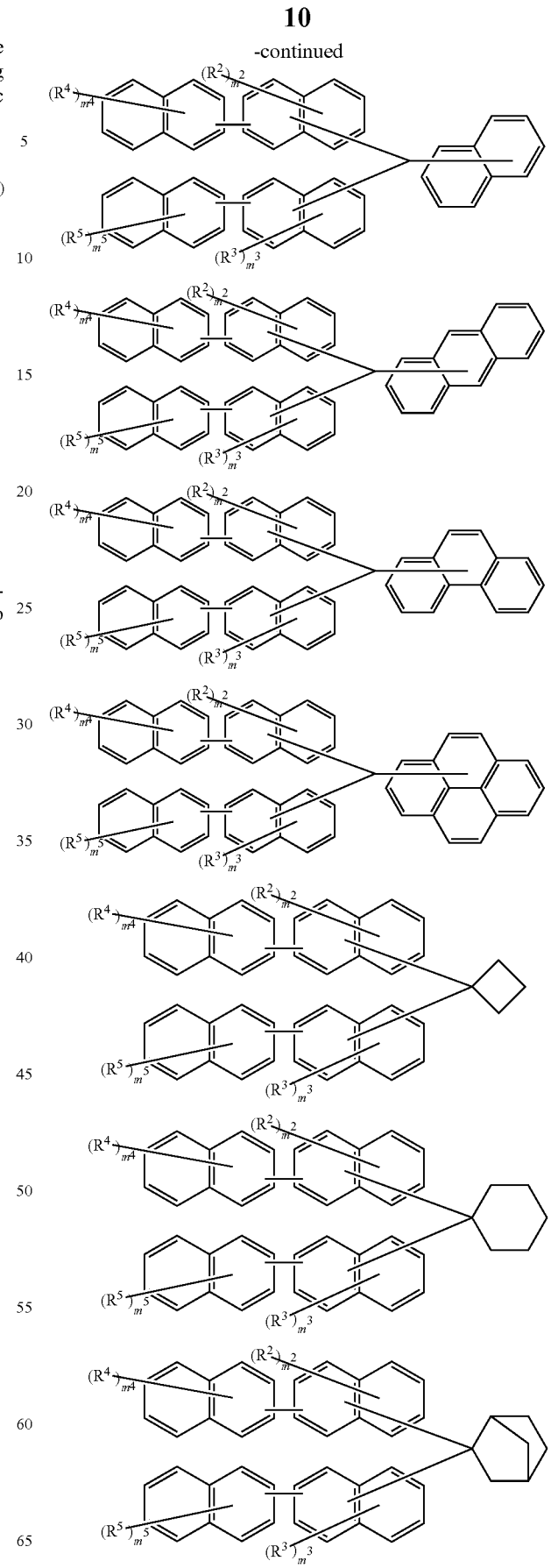

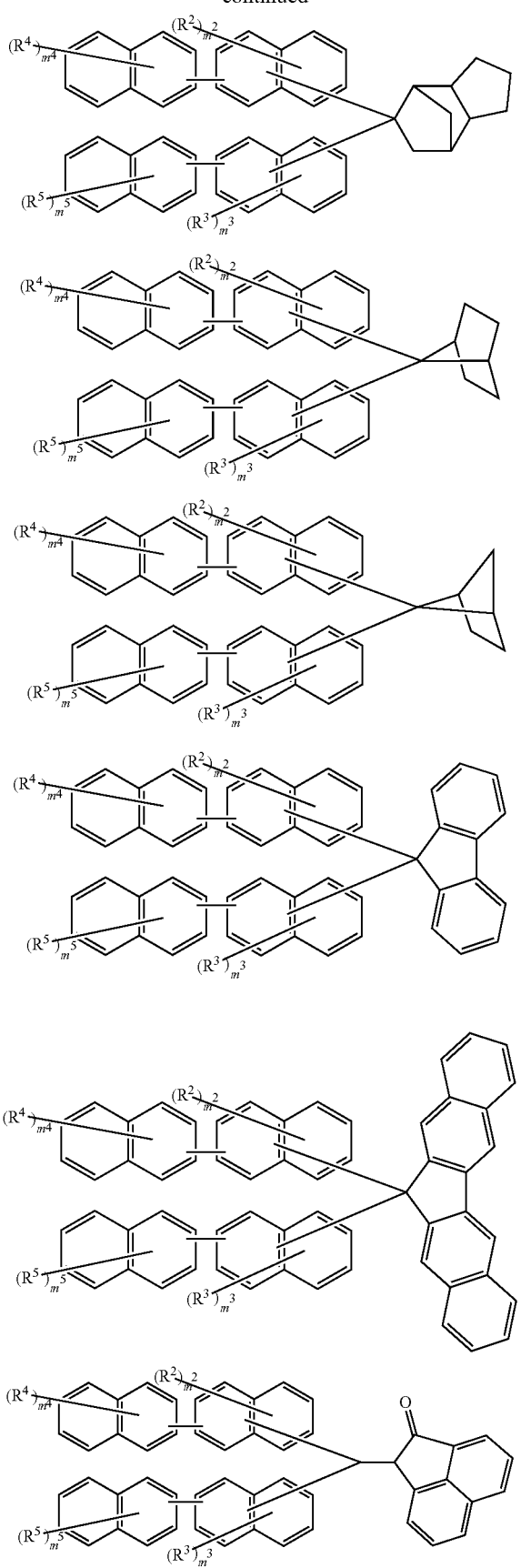
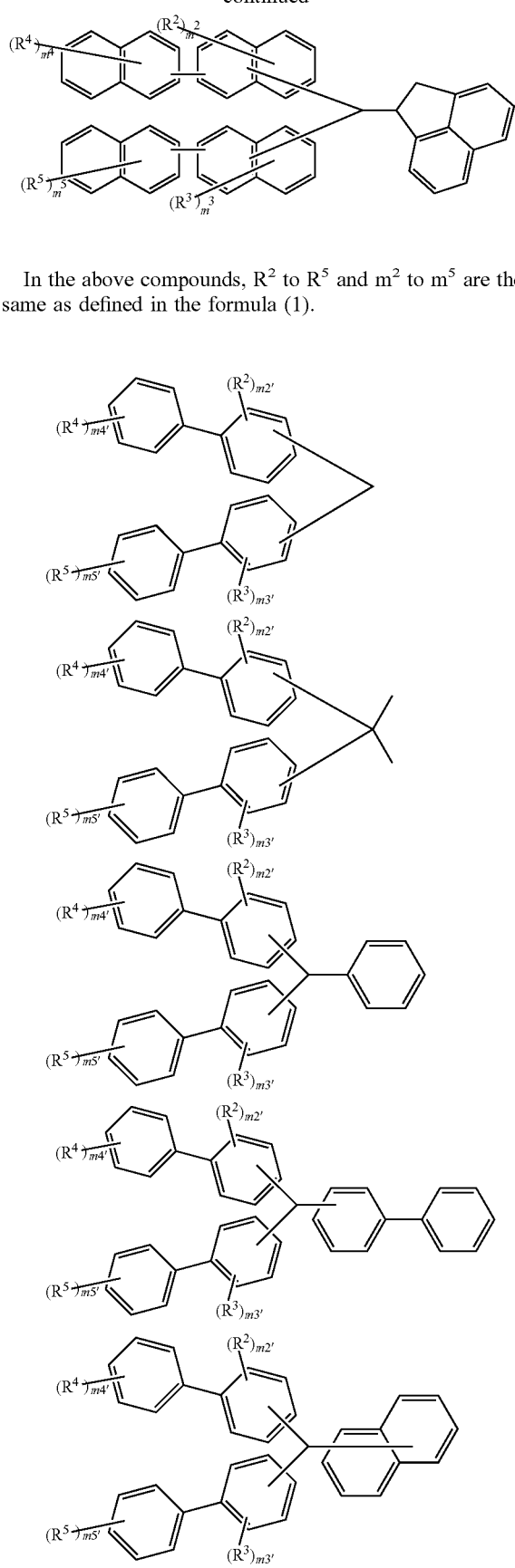
In the above compounds, $R^2$ to $R^5$ and $m^2$ to $m^5$ are the same as defined in the formula (1).

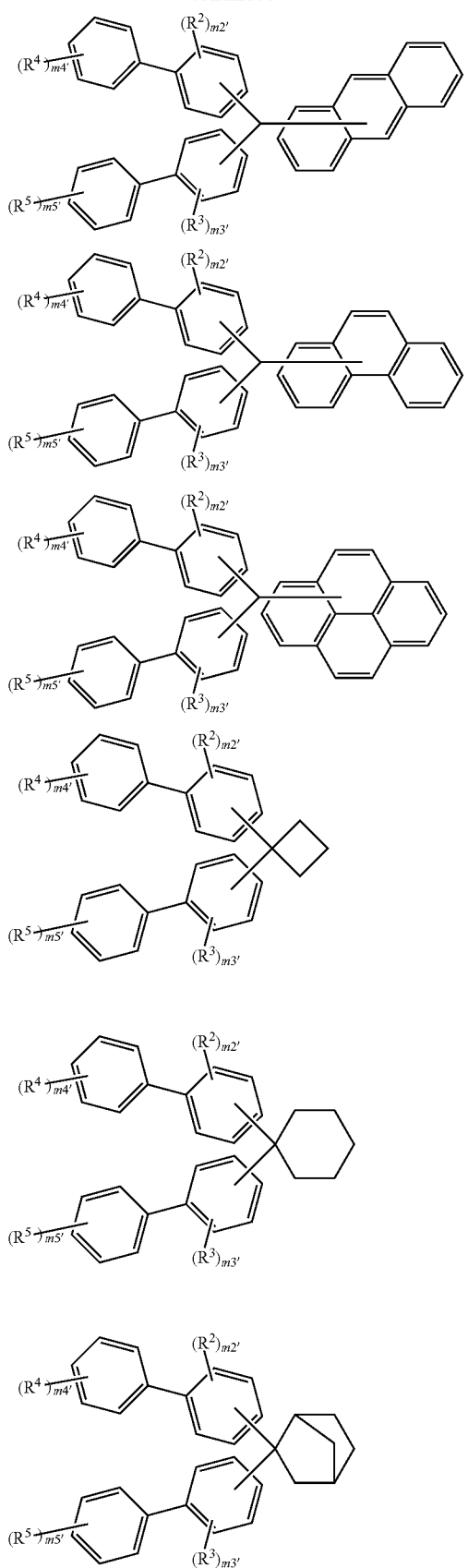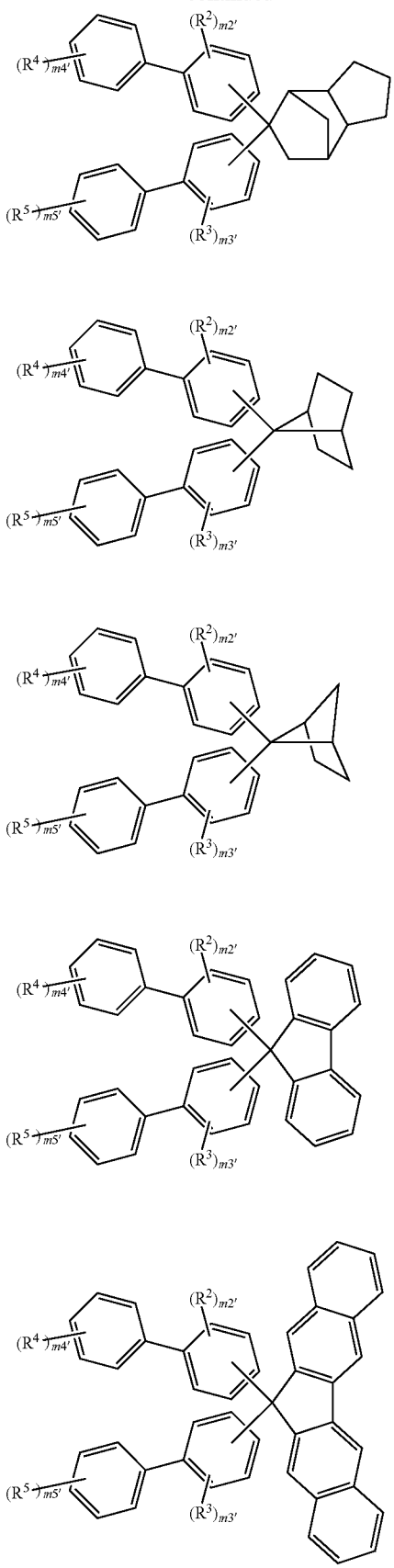

-continued
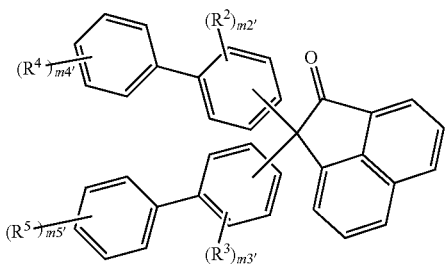
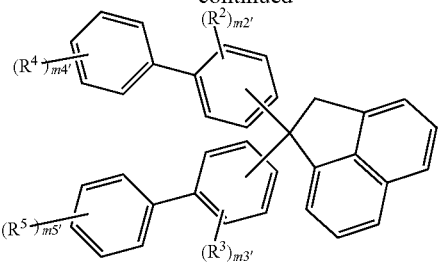
In the above compounds, $R^2$ to $R^5$ are the same as defined in the formula (1).
Each of $m^{2'}$ and $m^{3'}$ is independently an integer of 0 to 4, and each of $m^{4'}$ and $m^{5'}$ is independently an integer of 0 to 5, wherein at least one of $m^{4'}$ and $m^{5'}$ is an integer of 1 to 5, namely, $m^{4'}$ and $m^{5'}$ are not 0 at the same time.
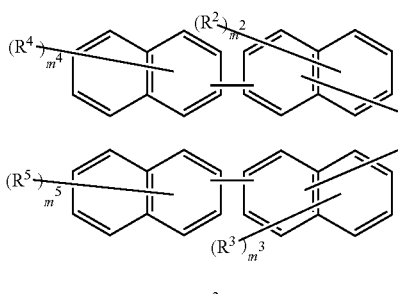
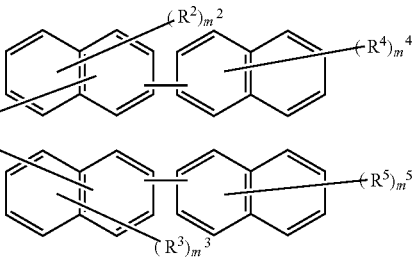
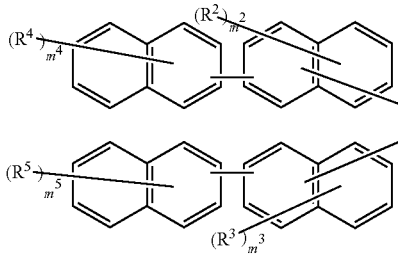
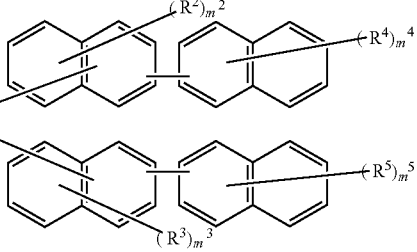
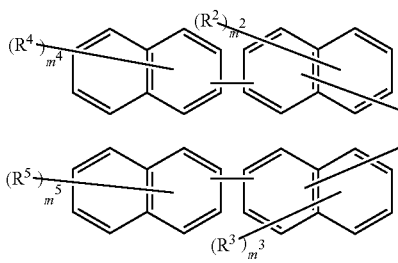
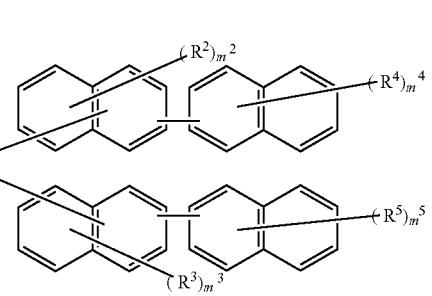
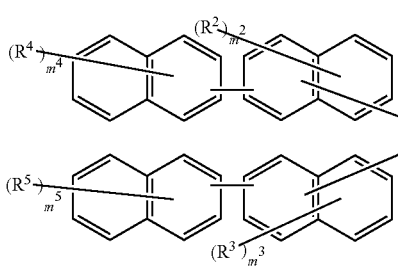
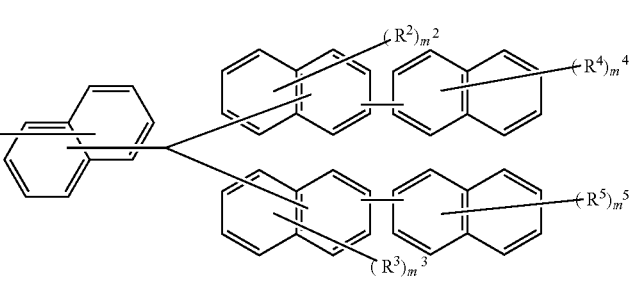

-continued
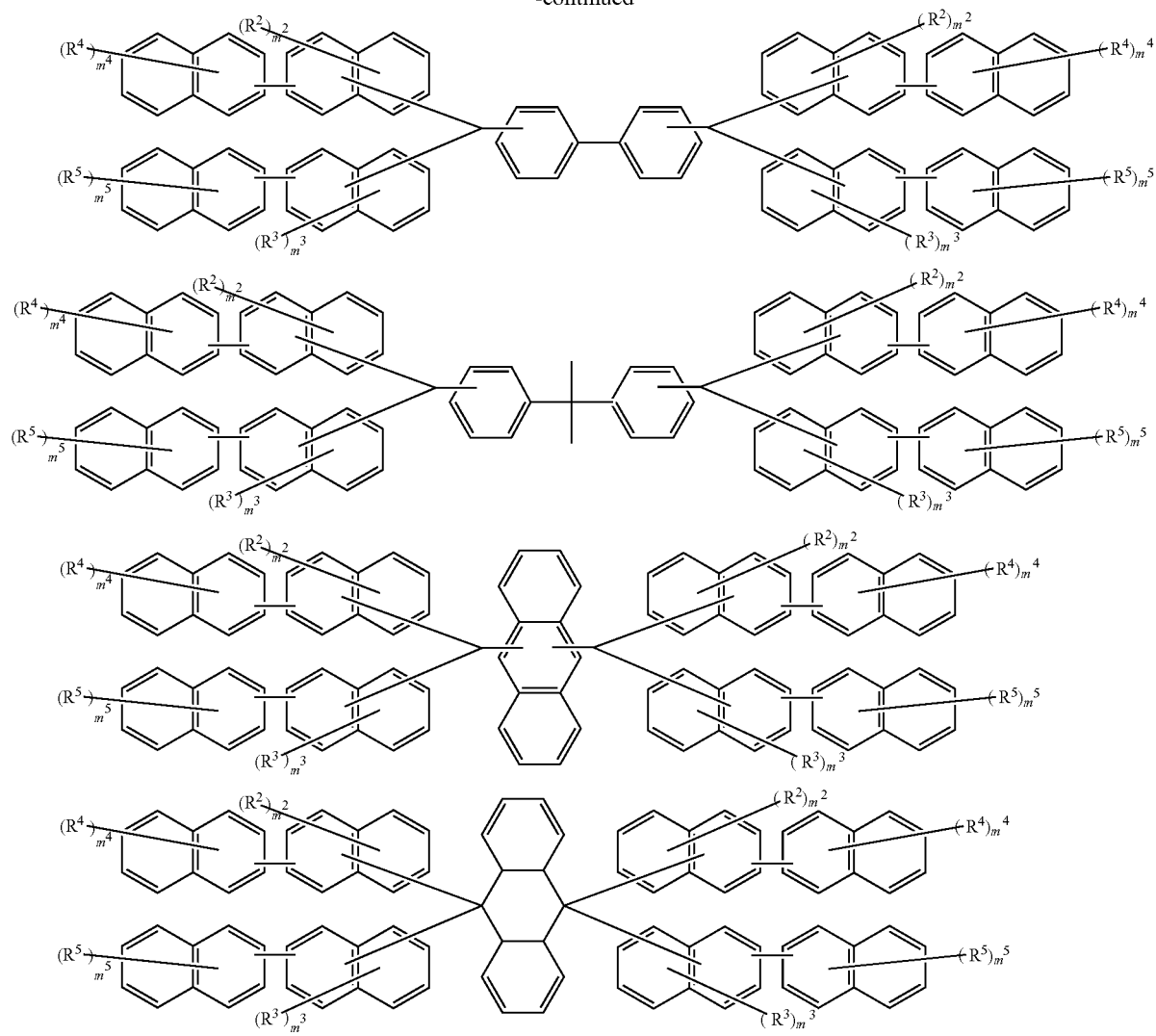
In the above compounds, $R^2$ to $R^5$ and $m^2$ to $m^5$ are the same as defined in the formula (1).
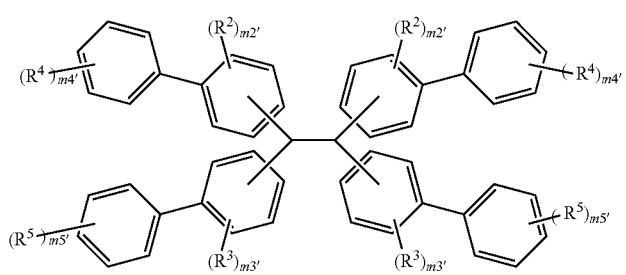

-continued
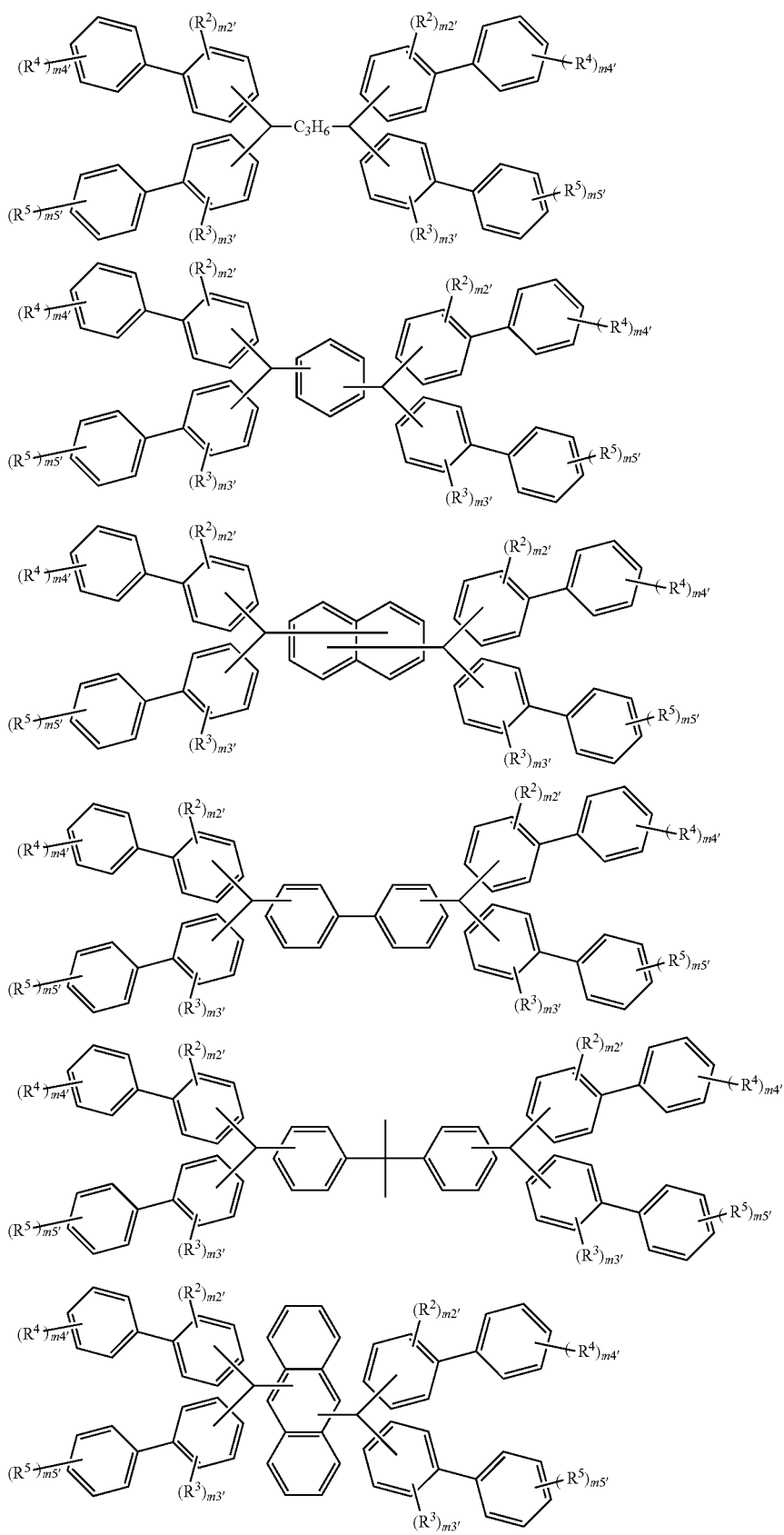

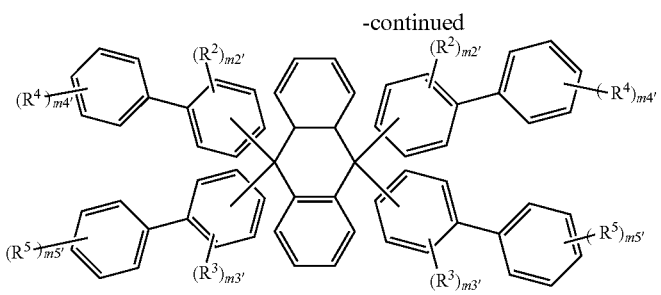
In the above compounds, $R^2$ to $R^5$ are the same as defined in the formula (1).
Each of $m^{2'}$ and $m^{3'}$ is independently an integer of 0 to 4, and each of $m^{4'}$ and $m^{5'}$ is independently an integer of 0 to 5, wherein at least one of $m^{4'}$ and $m^{5'}$ is an integer of 1 to 5, namely, $m^{4'}$ and $m^{5'}$ are not 0 at the same time.
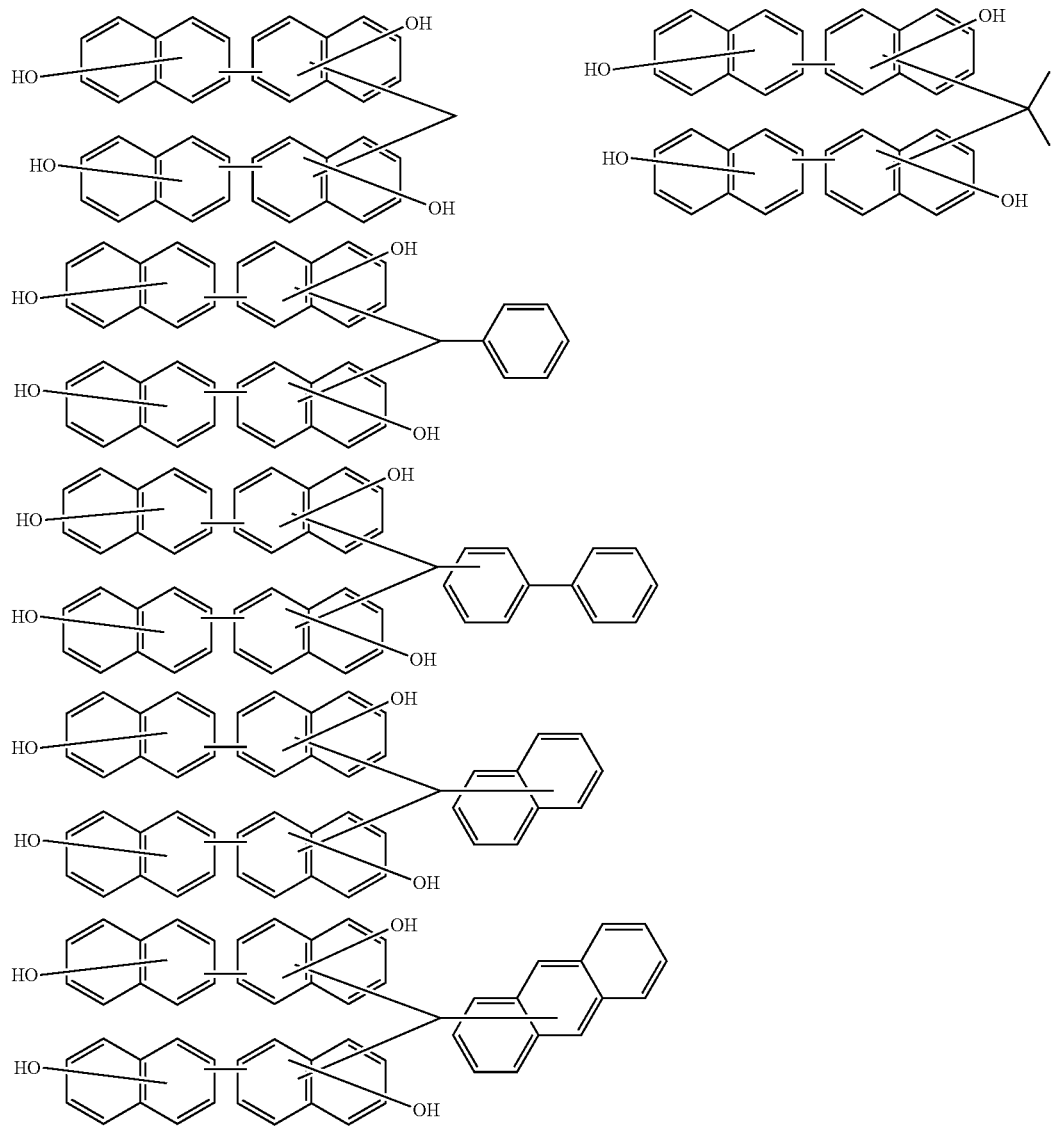

-continued
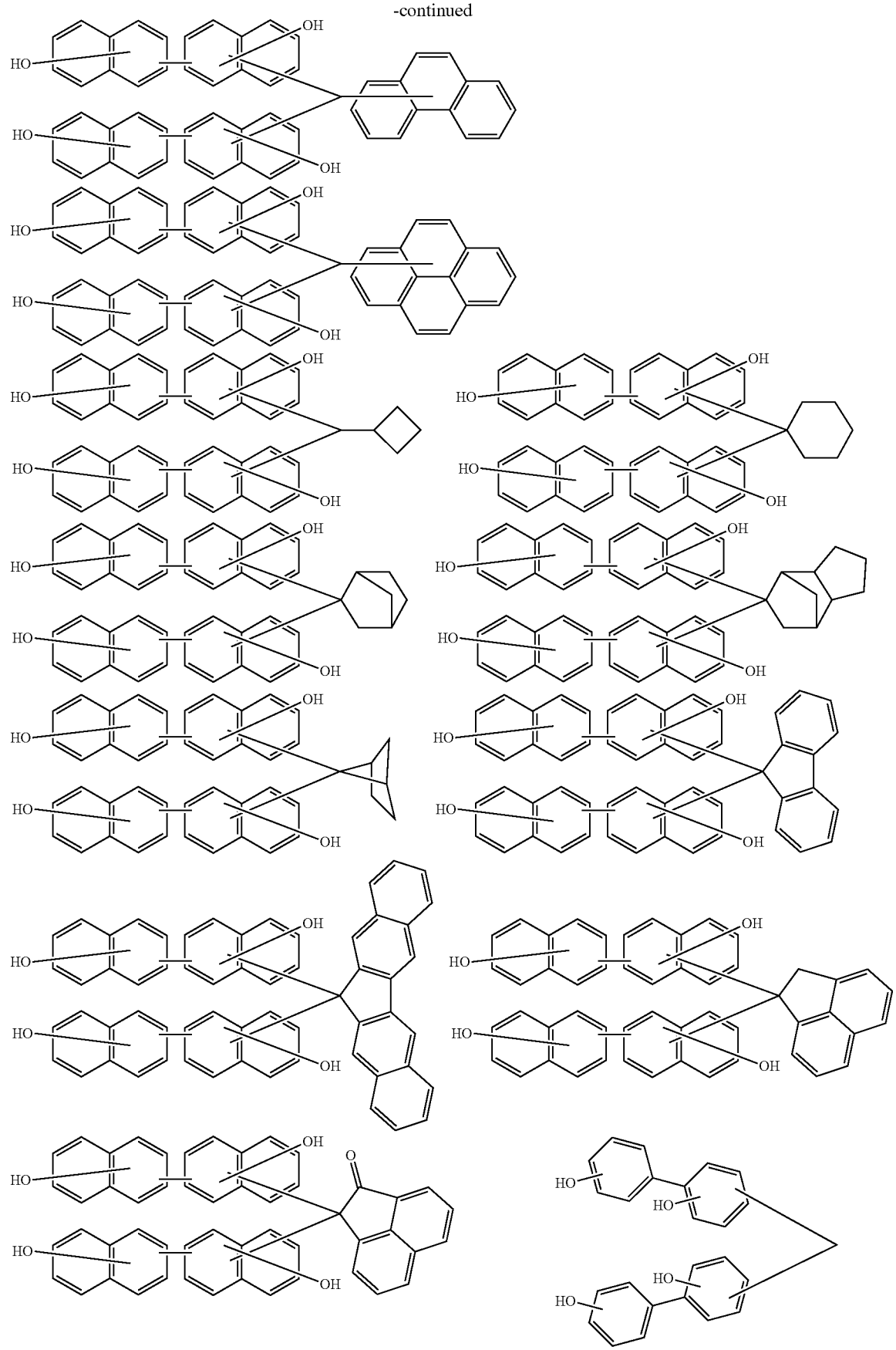

-continued
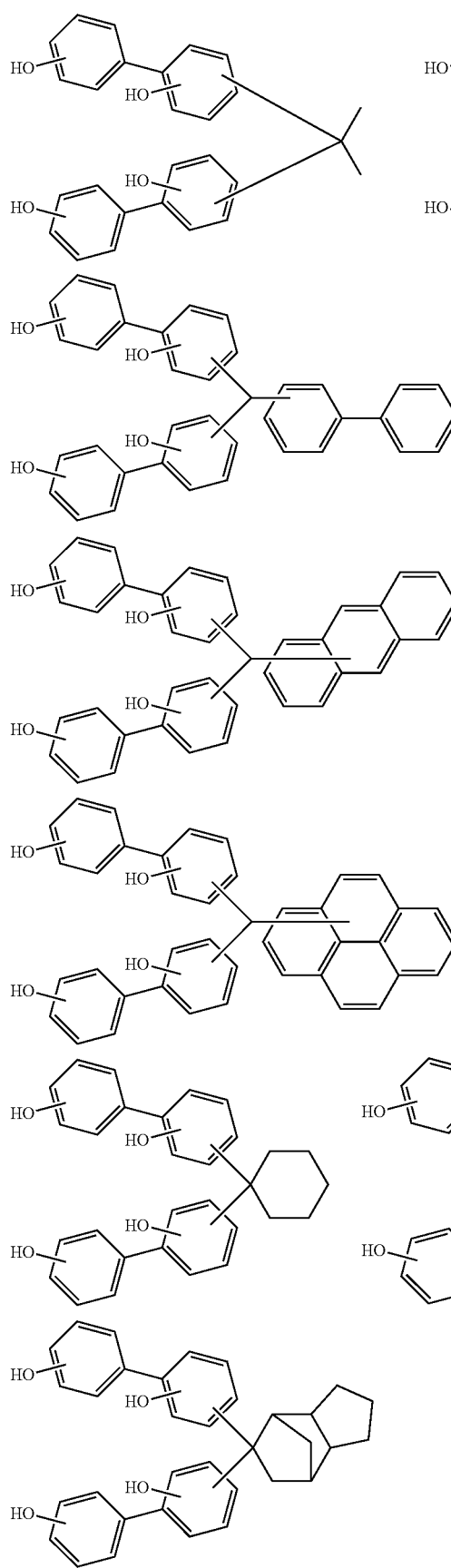
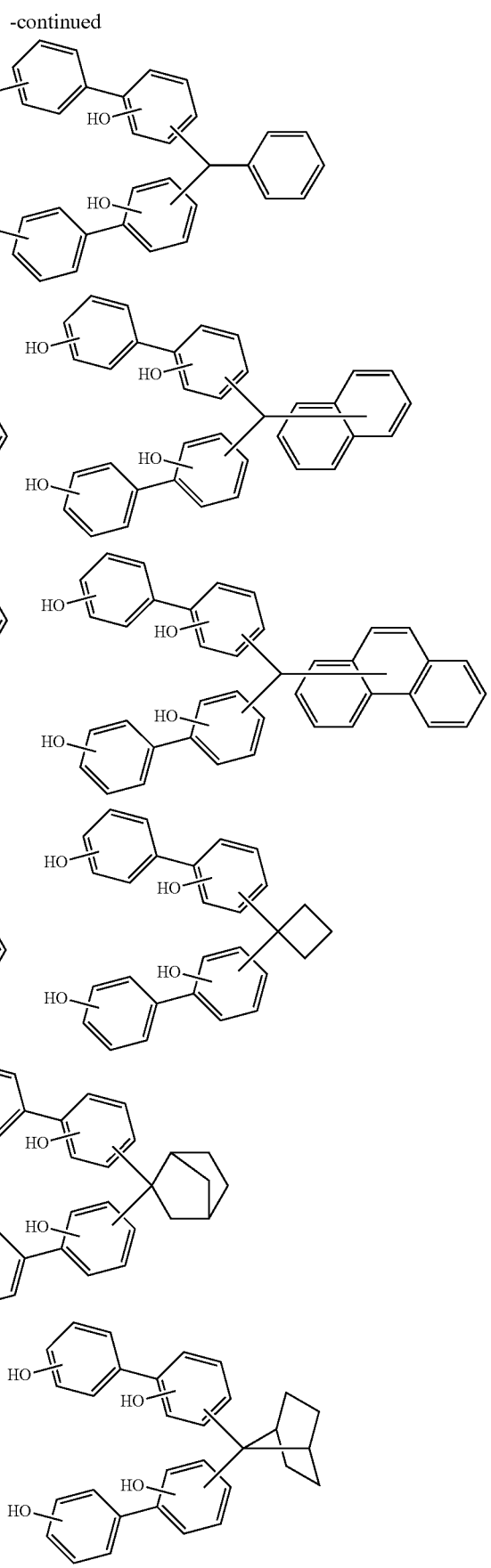

-continued
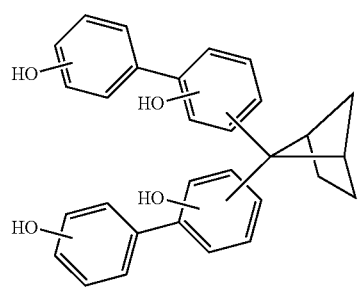
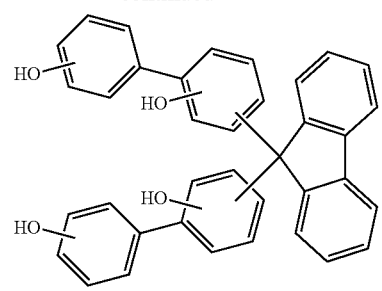
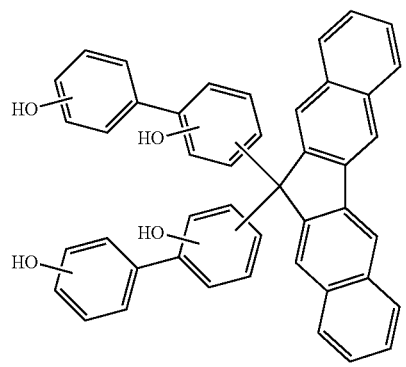
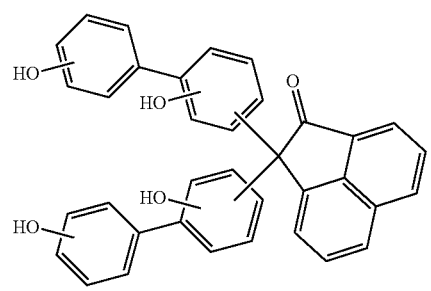
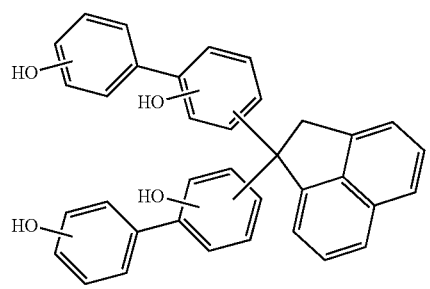
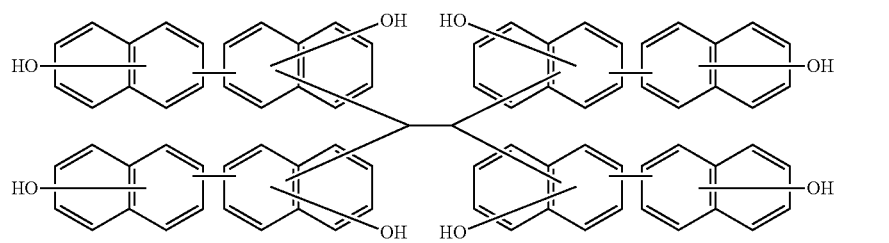
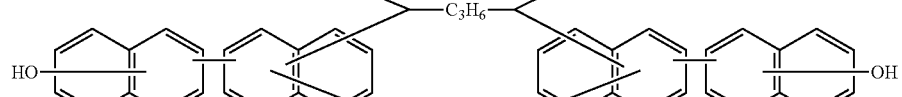
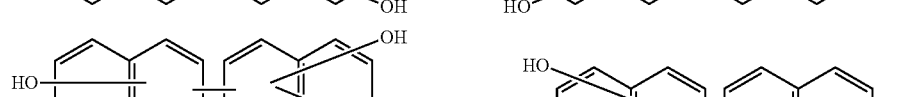
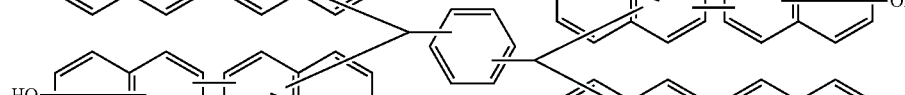

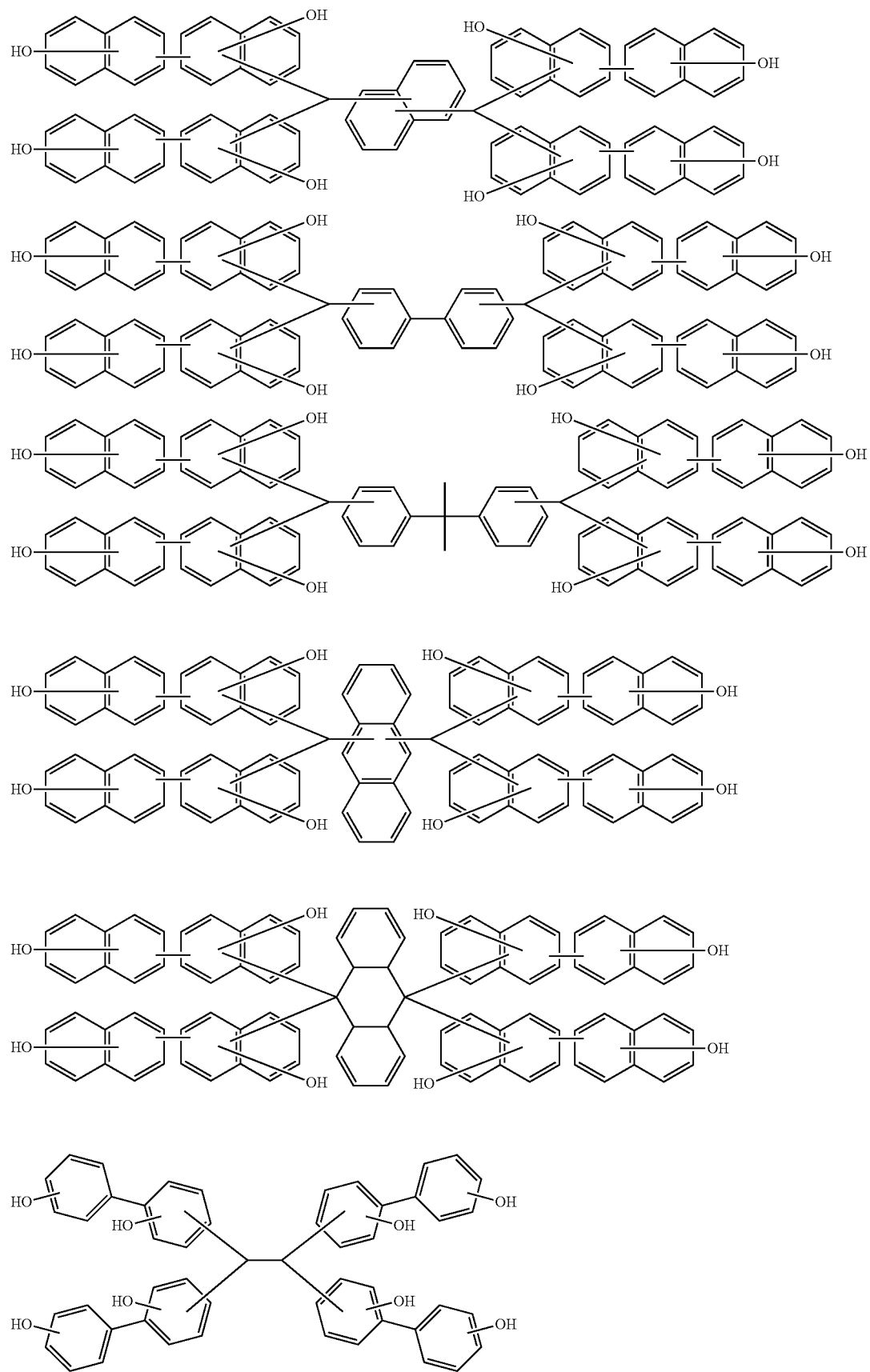

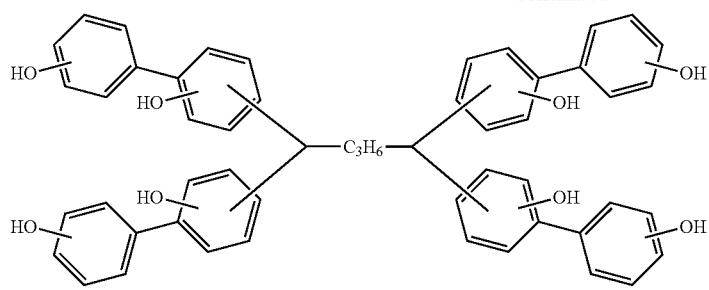
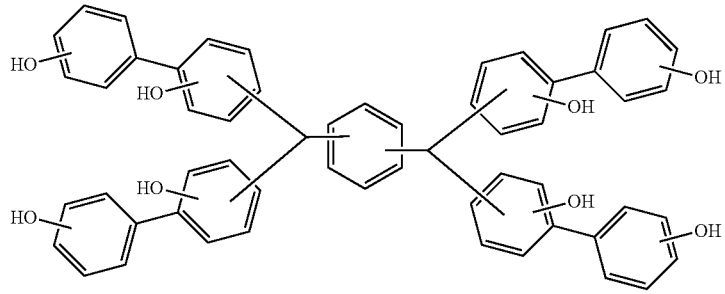
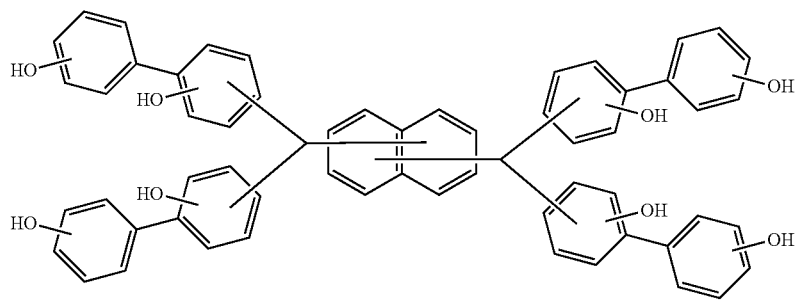
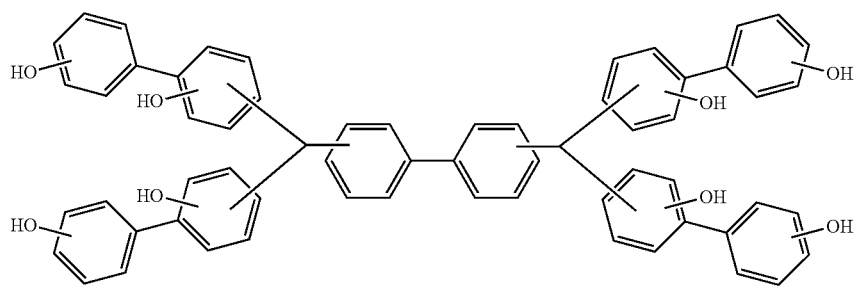
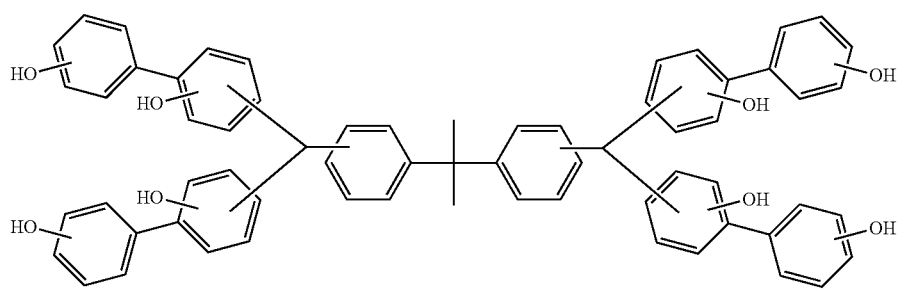

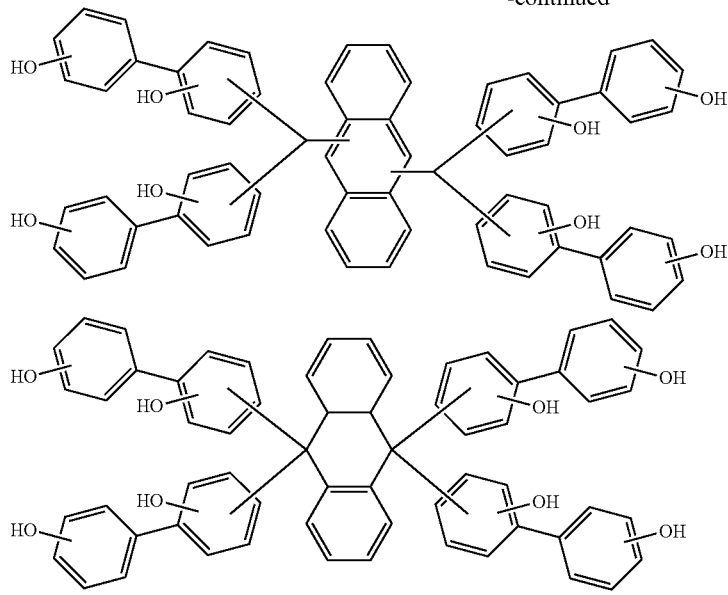

In the present embodiment, the compound represented by the formula (1) can be appropriately synthesized by applying a known method, and a synthesis method thereof is not particularly limited. For example, biphenols, bithiophenols, binaphthols, bithionaphthols or bianthracenols and the corresponding aldehydes or ketones can be subjected to a polycondensation reaction under ordinary pressure in the presence of an acid catalyst to thereby provide the compound represented by the formula (1). The reaction can also be performed under pressure, if necessary.

Examples of the biphenols include biphenol, methyl biphenol and methoxy binaphthol, but are not limited thereto. These can be used singly or in combinations of two or more thereof. Among them, biphenol is preferably used from the viewpoint of the stable supply of raw materials.

Examples of the bithiophenols include bithiophenol, methyl bithiophenol and methoxy bithiophenol, but are not limited thereto. These can be used singly or in combinations of two or more thereof. Among them, bithiophenol is preferably used from the viewpoint of the stable supply of raw materials.

Examples of the binaphthols include binaphthol, methyl binaphthol and methoxy binaphthol, but are not limited thereto. These can be used singly or in combinations of two or more thereof. Among them, binaphthol is preferably used from the viewpoints of increasing the carbon atom concentration and enhancing heat resistance.

Examples of the bithionaphthols include bithionaphthol, methyl bithionaphthol and methoxy bithionaphthol, but are not limited thereto. These can be used singly or in combinations of two or more thereof. Among them, bithionaphthol is preferably used from the viewpoints of increasing the carbon atom concentration and enhancing heat resistance.

Examples of the bianthracenols include bianthracenol, methyl bianthracenol and methoxy bianthracenol, but are not limited thereto. These can be used singly or in combinations of two or more thereof. Among them, bianthracenol is preferably used from the viewpoint of the stable supply of raw materials.

Examples of the aldehydes include, but are not particularly limited to the following, formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl)methane, bis(diformylphenyl)propane, or benzenetricarboxaldehyde is preferably used from the viewpoint of imparting a high heat resistance.

Examples of the ketones include acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone, but are not limited thereto. These can be used alone, or two or more thereof can be used in combination. Among them, cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used from the viewpoint of imparting a high heat resistance.

The acid catalyst for use in the above reaction can be appropriately selected from known ones and used, and is not particularly limited. Such an acid catalyst is an inorganic acid or an organic acid, as widely known, and examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, or solid acids such as tungstosilicic acid, tungstophosphoric acid, silicomolybdic acid, or phosphomolybdic acid, but are not limited thereto. Among them, organic acids and solid acids are preferable in terms of production, and hydrochloric acid or sulfuric acid is more preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials.

A reaction solvent may also be used during the above reaction. The reaction solvent that can be used is not particularly limited and is appropriately selected from known ones, as long as the reaction of the aldehydes or ketones to be used and the biphenols, bithiophenols, binaphthols, bithionaphthols or bianthracene diols to be used progresses. Examples thereof include water, methanol, ethanol, propanol, butanol, tetrahydrofuran, dioxane, ethylene glycol dimethyl ether, ethylene glycol diethyl ether, or a mixed solvent thereof. Herein, these solvents can be used alone, or two or more thereof can be used in combination.

In addition, the amount of the solvent to be used can be appropriately set depending on the types of raw materials to be used and the catalyst to be used, reaction conditions, and the like, and is not particularly limited, but the amount is preferably 0 to 2000 parts by mass based on 100 parts by mass of reaction raw materials. Furthermore, the reaction temperature in the above reaction can be appropriately selected depending on the reactivity of reaction raw materials, and is not particularly limited, but the reaction temperature usually ranges from 10 to 200° C.

In order to obtain the compound represented by the formula (1) of the present embodiment, the reaction temperature is preferably high and, specifically, preferably ranges from 60 to 200° C. Herein, the reaction method that can be used is appropriately selected from known methods, and is not particularly limited, but includes a method in which the biphenols, bithiophenols, binaphthols, bithionaphthols or bianthracene diols, the aldehydes or ketones, and the catalyst are charged at once, and a method in which the biphenols, bithiophenols, binaphthols, bithionaphthols or bianthracene diols, and the aldehydes or ketones are dropped in the presence of the catalyst. After completion of the polycondensation reaction, the resulting compound can be isolated according to an ordinary method, and the isolation method is not particularly limited. For example, in order to remove the unreacted raw materials and the catalyst present in the system, a common method in which the temperature in a reaction tank is raised to 130 to 230° C. to remove a volatile content at about 1 to 50 mmHg can be adopted to thereby provide an objective compound.

The reaction progresses under a preferable reaction condition in which 1 mol to an excess amount of the biphenols, bithiophenols, binaphthols, bithionaphthols or bianthracene diols and 0.001 to 1 mol of the acid catalyst are used, based on 1 mol of the aldehydes or ketones at ordinary pressure and at 50 to 150° C. for about 20 minutes to 100 hours.

After completion of the reaction, the objective compound can be isolated by a known method. For example, the objective compound, the compound represented by the formula (1), can be obtained by concentrating a reaction liquid, adding pure water thereto to precipitate a reaction product, cooling the resultant to room temperature followed by filtration for separation, drying a solid obtained by filtration, then separating the solid into the reaction product and a by-product for purification by column chromatography, and performing distilling off of the solvent, filtration and drying.

[Resin]

A resin of the present embodiment is a resin obtained by using the compound represented by the formula (1) as a monomer. The resin of the present embodiment has a structure represented by formula (2).

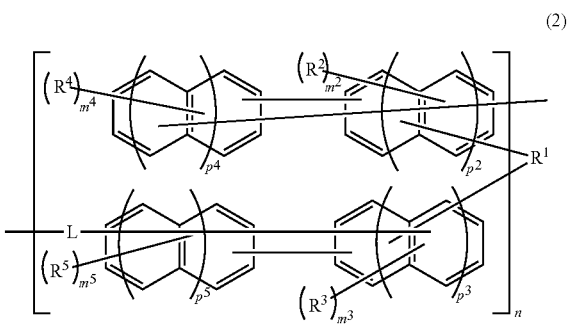

In the formula (2), $R^1$ is a 2n-valent group having 1 to 30 carbon atoms, and examples of the group include those having a linear hydrocarbon group, a branched hydrocarbon group or a cyclic hydrocarbon group. Herein, the cyclic hydrocarbon group also includes a bridged cyclic hydrocarbon group. The 2n-valent group may also have an aromatic group having 6 to 30 carbon atoms.

The 2n-valent group may also have a double bond. The group may also have a hetero atom.

Each of $R^2$ to $R^5$ is independently a linear, branched or cyclic alkyl group having 1 to 10 carbon atoms, an aryl group having 6 to 10 carbon atoms, an alkenyl group having 2 to 10 carbon atoms, a thiol group or a hydroxyl group, wherein at least one $R^4$ and/or at least one $R^5$ is a hydroxyl group and/or a thiol group.

L is a single bond, or a linear or branched alkylene group having 1 to 20 carbon atoms.

Each of $m^2$ and $m^3$ is independently an integer of 0 to 8, and each of $m^4$ and $m^5$ is independently an integer of 0 to 9, wherein at least one of $m^4$ and $m^5$ is an integer of 1 to 9, namely, $m^4$ and $m^5$ are not 0 at the same time.

n is an integer of 1 to 4.

Each of $p^2$ to $p^5$ is independently an integer of 0 to 2.

In the resin of the present embodiment, from the viewpoint of imparting availability of raw materials and heat resistance, it is preferable that n is 1 and $R^1$ is a group represented by $R^A$—$R^B$, wherein $R^A$ is a methine group and $R^B$ is an aryl group having 7 or more carbon atoms. Examples of the aryl group having 7 or more carbon atoms include, but not limited to the following, biphenyl, naphthalene, anthracene, pyrene, perylene, fluorene and triphenylmethane.

The resin of the present embodiment is obtained by, for example, reacting the compound represented by the formula (1) with a compound having crosslinking reactivity.

The compound having crosslinking reactivity is not particularly limited as long as it can provide an oligomer or a polymer of the compound represented by the formula (1), and known one can be used therefor. Specific examples thereof include aldehyde, ketone, carboxylic acid, carboxylic halide, a halogen-containing compound, an amino compound, an imino compound, isocyanate, and an unsaturated hydrocarbon group-containing compound, but are not limited thereto.

Specific examples of the resin of the present embodiment include, but are not limited to the following, a novolac resin obtained by a condensation reaction of the compound represented by the formula (1) with an aldehyde as the compound having crosslinking reactivity, or the like.

Herein, examples of the aldehyde for use in forming the novolac resin of the compound represented by the formula (1) include formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural, but are not limited thereto. Among them, formaldehyde is preferable. Herein, these aldehydes can be used alone, or two or more thereof can be used in combination. In addition, the amount of the aldehydes to be used is not particularly limited, but the amount is preferably 0.2 to 5 mol and more preferably 0.5 to 2 mol, based on 1 mol of the compound represented by the formula (1).

A catalyst can also be used in the condensation reaction of the compound represented by the formula (1) with an aldehyde. The acid catalyst that can be here used is appropriately selected from known ones, and is not particularly limited. Such an acid catalyst is an inorganic acid or an organic acid, as widely known, and examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, or solid acids such as tungstosilicic acid, tungstophosphoric acid, silicomolybdic acid, or phosphomolybdic acid, but are not limited thereto. Among them, organic acids and solid acids are preferable in terms of production, and hydrochloric acid or sulfuric acid is more preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials. Herein, in the case of copolymerization with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, and limonene, no aldehydes may be used.

A reaction solvent can also be used in the condensation reaction of the compound represented by the formula (1) with an aldehyde. The reaction solvent in the polycondensation, which can be used, is appropriately selected from known ones, and is not particularly limited, but examples thereof include water, methanol, ethanol, propanol, butanol, tetrahydrofuran, dioxane, or a mixed solvent thereof. Herein, these solvents can be used alone, or two or more thereof can be used in combination.

In addition, the amount of the solvent to be used can be appropriately set depending on the types of raw materials to be used and the catalyst to be used, reaction conditions, and the like, and is not particularly limited, but the amount preferably ranges from 0 to 2000 parts by mass based on 100 parts by mass of reaction raw materials. Furthermore, the reaction temperature can be appropriately selected depending on the reactivity of reaction raw materials, and is not particularly limited, but the reaction temperature usually ranges from 10 to 200° C. Herein, the reaction method that can be used is appropriately selected from known methods, and is not particularly limited, but includes a method in which the compound represented by the formula (1), the aldehydes, and the catalyst are charged at once, and a method in which the compound represented by the formula (1) and the aldehydes are dropped in the presence of the catalyst.

After completion of the polycondensation reaction, the resulting compound can be isolated according to an ordinary method, and the isolation method is not particularly limited. For example, in order to remove the unreacted raw materials and the catalyst present in the system, a common method in which the temperature in a reaction tank is raised to 130 to 230° C. to remove a volatile content at about 1 to 50 mmHg can be adopted to thereby provide an objective novolac resin.

Herein, the resin of the present embodiment may be a homopolymer of the compound represented by the formula (1), or may be a copolymer thereof with other phenols. Examples of the copolymerizable phenols include phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol, but are not limited thereto.

In addition, the resin of the present embodiment may be one obtained by copolymerization with a polymerizable monomer other than the above-described other phenols. Examples of such a copolymerizable monomer include naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornaene, pinene, and limonene, but are not limited thereto. Herein, the resin of the present embodiment may be a bi or higher functional (for example, bi to tetra) copolymer of the compound represented by the formula (1) with phenols, may be a bi or higher functional (for example, bi to tetra) copolymer of the compound represented by the formula (1) with the above-described copolymerizable monomer, or may be a ter or higher (for example, ter to tetra) copolymer of the compound represented by the formula (1), the above-described phenols, and the above-described copolymerizable monomer.

Herein, the molecular weight of the resin of the present embodiment is not particularly limited, and the weight average molecular weight (Mw) in terms of polystyrene is preferably 500 to 30,000, and more preferably 750 to 20,000. In addition, the resin of the present embodiment preferably has a dispersity (weight average molecular weight Mw/number average molecular weight Mn) in a range from 1.2 to 7 from the viewpoints of improving a crosslinking efficiency and suppressing a volatile component during baking. Herein, the Mn can be determined by a method in Examples described later.

The compound represented by the formula (1) and/or the resin obtained by using the compound as a monomer preferably has a high solubility in the solvent from the viewpoint of making the application of a wet process easier. More specifically, when the solvent is 1-methoxy-2-propanol (PGME) and/or propylene glycol monomethyl ether acetate (PGMEA), such a compound and/or resin preferably have/has a solubility of 10% by mass or more in the solvent. Herein, the solubility in PGME and/or PGMEA is defined as "Mass of resin/(Mass of resin+Mass of solvent)×100 (% by mass)". For example, in the case where 10 g of the compound represented by the formula (1) and/or the resin obtained by using the compound as a monomer is evaluated to be dissolved in 90 g of PGMEA, the solubility of the compound represented by the formula (1) and/or the resin obtained by using the compound as a monomer in PGMEA is "10% by mass or more", and in the case where the compound and/or the resin is evaluated not to be dissolved, the solubility is "less than 10% by mass".

[Material for Forming Underlayer Film for Lithography]

A material for forming an underlayer film for lithography of the present embodiment contains the compound represented by the formula (1) or the resin obtained by using the compound as a monomer. That is, the material for forming an underlayer film for lithography of the present embodiment contains at least the compound or the resin of the present embodiment. The material for forming an underlayer film for lithography of the present embodiment has such a configuration, and therefore can be applied to a wet process and is excellent in heat resistance and etching resistance. Furthermore, since the material for forming an underlayer film for lithography of the present embodiment contains the compound or the resin, the material can be used to form an underlayer film whose degradation is suppressed at high-temperature baking and which is also excellent in etching resistance to oxygen plasma etching or the like. Furthermore, the material for forming an underlayer film for lithography of the present embodiment is also excellent in adhesiveness with a resist layer and therefore can form an excellent resist pattern.

The material for forming an underlayer film for lithography of the present embodiment may contain, if necessary, other component such as an organic solvent, a crosslinking agent, and an acid generator, other than the compound represented by the formula (1) and/or the resin obtained by using the compound as a monomer. Hereinafter, these optional components will be described.

The material for forming an underlayer film for lithography of the present embodiment may contain an organic solvent. As the organic solvent, a known solvent can be appropriately used as long as it dissolves at least the compound represented by the formula (1) and/or the resin obtained by using the compound as a monomer.

Specific examples of the organic solvent include ketone-based solvents such as acetone, methyl ethyl ketone, methyl isobutyl ketone and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, ethyl lactate, methyl methoxypropionate and methyl hydroxyisobutyrate; alcohol-based solvents such as methanol, ethanol, isopropanol and 1-ethoxy-2-propanol; and aromatic hydrocarbons such as toluene, xylene and anisole, but are not limited thereto. These organic solvents can be used singly or in combinations of two or more thereof.

Among the organic solvents, preferable are cyclohexanone, propylene glycol monomethyl ether, propylene glycol monomethyl ether acetate, ethyl lactate, methyl hydroxyisobutyrate, and anisole, in terms of safety.

When the material for forming an underlayer film for lithography of the present embodiment contains the organic solvent, the content of the compound represented by the formula (1) and/or the content of the resin obtained by using the compound as a monomer is not particularly limited, but is preferably 1 to 70 parts by mass, more preferably 2 to 50 parts by mass, further preferably 5 to 40 parts by mass, based on 100 parts by mass of the total amount of the components including the organic solvent.

The material for forming an underlayer film for lithography of the present embodiment may contain, if necessary, a crosslinking agent from the viewpoint of suppression of intermixing, and the like. Specific examples of the crosslinking agent usable in the present embodiment include a melamine compound, a guanamine compound, a glycoluril compound, a urea compound, an epoxy compound, a thioepoxy compound, an isocyanate compound, an azide compound, and a compound including a double bond such as an alkenyl ether group, these compounds being substituted with at least one group selected from a methylol group, an alkoxymethyl group and an acyloxymethyl group, as a substituent (crosslinkable group), but are not limited thereto. Herein, these crosslinking agents can be used singly or in combinations of two or more thereof. Such a crosslinking agent can also be used as an additive. Herein, the crosslinkable group may also be introduced as a pendant group into a polymer side chain of the compound represented by the formula (1) and/or the resin obtained by using the compound as a monomer. A compound including a hydroxy group can also be used as the crosslinking agent.

Specific examples of the melamine compound include, but are not limited to the following, hexamethylolmelamine, hexamethoxymethylmelamine, a compound in which 1 to 6 methylol groups in hexamethylolmelamine are methoxymethylated, or mixtures thereof, and hexamethoxyethylmelamine, hexaacyloxymethylmelamine, a compound in which 1 to 6 methylol groups in hexamethylolmelamine are acyloxymethylated, or mixtures thereof. Specific examples of the epoxy compound include, but are not limited to the following, tris(2,3-epoxypropyl)isocyanurate, trimethylolmethane triglycidyl ether, trimethylolpropane triglycidyl ether, and triethylolethane triglycidyl ether.

Specific examples of the guanamine compound include, but are not limited to the following, tetramethylolguanamine, tetramethoxymethylguanamine, a compound in which 1 to 4 methylol groups in tetramethylolguanamine are methoxymethylated, or mixtures thereof, and tetramethoxyethylguanamine, tetraacyloxyguanamine, a compound in which 1 to 4 methylol groups in tetramethylolguanamine are acyloxymethylated, or mixtures thereof. Specific examples of the glycoluril compound include, but are not limited to the following, tetramethylolglycoluril, tetramethoxyglycoluril, tetramethoxymethylglycoluril, a compound in which 1 to 4 methylol groups in tetramethylolglycoluril are methoxymethylated, or mixtures thereof, and a compound in which 1 to 4 methylol groups in tetramethylolglycoluril are acyloxymethylated, or mixtures thereof. Specific examples of the urea compound include, but are not limited to the following, tetramethylolurea, tetramethoxymethylurea, a compound in which 1 to 4 methylol groups in tetramethylolurea are methoxymethylated, or mixtures thereof, and tetramethoxyethylurea.

Specific examples of the compound including an alkenyl ether group include, but are not limited to the following, ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

In the material for forming an underlayer film for lithography according to the present embodiment, the content of the crosslinking agent is not particularly limited, but the content is preferably 5 to 50 parts by mass and more preferably 10 to 40 parts by mass, based on 100 parts by mass of the compound represented by the formula (1) and the resin obtained by using the compound as a monomer. The content is set within the above preferable range to result in tendencies to suppress the occurrence of the mixing phenomenon with the resist layer, and to result in tendencies to enhance an antireflective effect and improve film formability after crosslinking.

The material for forming an underlayer film for lithography of the present embodiment may also contain, if necessary, an acid generator from the viewpoint of further promoting a crosslinking reaction by heat. As the acid generator, one for generating an acid by pyrolysis and one for generating an acid by light irradiation are known, and any of them can be used.

Examples of the acid generator include:
1) an onium salt of the following general formula (P1a-1), (P1a-2), (P1a-3) or (P1b),
2) a diazomethane derivative of the following general formula (P2),
3) a glyoxime derivative of the following general formula (P3),
4) a bissulfone derivative of the following general formula (P4),
5) a sulfonic acid ester of an N-hydroxyimide compound of the following general formula (P5),
6) a β-ketosulfonic acid derivative,
7) a disulfone derivative,
8) a nitrobenzylsulfonate derivative, and
9) a sulfonic acid ester derivative, but are not limited thereto. Herein, these acid generators can be used alone, or two or more thereof can be used in combination.

In the above formulae, each of $R^{101a}$, $R^{101b}$ and $R^{101c}$ independently represents a linear, branched or cyclic alkyl group, alkenyl group, oxoalkyl group or oxoalkenyl group having 1 to 12 carbon atoms; an aryl group having 6 to 20 carbon atoms; or an aralkyl group or aryloxoalkyl group having 7 to 12 carbon atoms, and a part or all of hydrogen atoms of these groups may be substituted with an alkoxy group or the like. In addition, $R^{101b}$ and $R^{101c}$ may form a ring, and if forming a ring, each of $R^{101b}$ and $R^{101c}$ independently represents an alkylene group having 1 to 6 carbon atoms. $K^-$ represents a non-nucleophilic counter ion. $R^{101d}$, $R^{101e}$, $R^{101f}$ and $R^{101g}$ are represented by each independently adding a hydrogen atom to $R^{101a}$, $R^{101b}$ and $R^{101c}$, $R^{101d}$ and $R^{101e}$, and $R^{101d}$, $R^{101e}$ and $R^{101f}$ may form a ring, and if forming a ring, $R^{101d}$ and $R^{101e}$, and $R^{101d}$, $R^{101e}$ and $R^{101f}$ represent an alkylene group having 3 to 10 carbon atoms, or a heteroaromatic ring having therein the nitrogen atom(s) in the formula.

$R^{101a}$, $R^{101b}$, $R^{101c}$, $R^{101d}$, $R^{101e}$, $R^{101f}$ and $R^{101g}$ described above may be the same or different from one another. Specifically, examples of the alkyl group include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methyl cyclohexyl group, a cyclohexylmethyl group, a norbornyl group, and an adamantyl group. Examples of the alkenyl group include, but are not limited to the following, a vinyl group, an allyl group, a propenyl group, a butenyl group, a hexenyl group, and a cyclohexenyl group. Examples of the oxoalkyl group can include, but are not limited to the following, a 2-oxocyclopentyl group, a 2-oxocyclohexyl group, a 2-oxopropyl group, a 2-cyclopentyl-2-oxoethyl group, a 2-cyclohexyl-2-oxoethyl group, and a 2-(4-methylcyclohexyl)-2-oxoethyl group. Examples of the oxoalkenyl group include, but are not limited to the following, a 2-oxo-4-cyclohexenyl group and a 2-oxo-4-propenyl group. Examples of the aryl group include, but are not limited to the following, a phenyl group, a naphthyl group, alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group; alkylnaphthyl groups such as a methylnaphthyl group and an ethylnaphthyl group; alkoxynaphthyl groups such as a methoxynaphthyl group and an ethoxynaphthyl group; dialkylnaphthyl groups such as a dimethylnaphthyl group and a diethylnaphthyl group; and dialkoxynaphthyl groups such as a dimethoxynaphthyl group and a diethoxynaphthyl group. Examples of the aralkyl group include, but are not limited to the following, a benzyl group, a phenylethyl group, and a phenethyl group. Examples of the aryloxoalkyl group include, but are not limited to the following, 2-aryl-2-oxoethyl groups such as a 2-phenyl-2-oxoethyl group, a 2-(1-naphthyl)-2-oxoethyl group, and a 2-(2-naphthyl)-2-oxoethyl group. Examples of the non-nucleophilic counter ion, $K^-$, include, but are not limited to the following, halide ions such as a chloride ion and a bromide ion; fluoroalkyl sulfonates such as triflate, 1,1,1-trifluoroethane sulfonate, and nonafluorobutane sulfonate; aryl sulfonates such as tosylate, benzene sulfonate, 4-fluorobenzene sulfonate, and 1,2,3,4,5-pentafluorobenzene sulfonate; and alkyl sulfonates such as mesylate and butane sulfonate.

In the case where $R^{101d}$, $R^{101e}$, $R^{101f}$ and $R^{101g}$ are each a heteroaromatic ring having the nitrogen atom(s) in the formula, examples of the heteroaromatic ring include imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivative, and uridine derivatives.

The onium salts of the formula (P1a-1) and the formula (P1a-2) have functions as a photo acid generator and a thermal acid generator. The onium salt of the formula (P1a-3) has a function as a thermal acid generator.

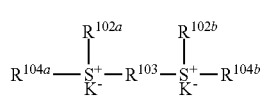
(P1b)

In the formula (P1b), each of $R^{102a}$ and $R^{102b}$ independently represents a linear, branched or cyclic alkyl group having 1 to 8 carbon atoms. $R^{103}$ represents a linear, branched or cyclic alkylene group having 1 to 10 carbon atoms. Each of $R^{104a}$ and $R^{104b}$ independently represents a 2-oxoalkyl group having 3 to 7 carbon atoms. $K^-$ represents a non-nucleophilic counter ion.

Specific examples of $R^{102a}$ and $R^{102b}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methyl cyclohexyl group, and a cyclohexylmethyl group. Specific examples of $R^{103}$ include, but are not limited to the following, a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Specific examples of $R^{104a}$ and $R^{104b}$ include, but are not limited to the following, a 2-oxopropyl group, a 2-oxocyclopentyl group, a 2-oxocyclohexyl group, and a 2-oxocycloheptyl group. $K^-$ includes the same as those described in the formula (P1a-1), (P1a-2) and (P1a-3).

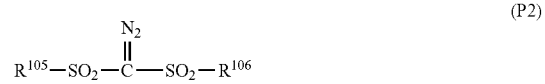
(P2)

In the formula (P2), each of $R^{105}$ and $R^{106}$ independently represents a linear, branched or cyclic alkyl group or halogenated alkyl group having 1 to 12 carbon atoms, an aryl group or halogenated aryl group having 6 to 20 carbon atoms, or an aralkyl group having 7 to 12 carbon atoms.

Examples of the alkyl group in each of $R^{105}$ and $R^{106}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. Examples of the halogenated alkyl group include, but are not limited to the following, a trifluoromethyl group, a 1,1,1-trifluoroethyl group, a 1,1,1-trichloroethyl group, and a nonafluorobutyl group. Examples of the aryl group include, but are not limited to the following, alkoxyphenyl groups such as a phenyl group, a p-methoxyphenyl group, a m-methoxyphenyl group, an o-methoxyphenyl group, an ethoxyphenyl group, a p-tert-butoxyphenyl group, and a m-tert-butoxyphenyl group; and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Examples of the halogenated aryl group include, but are not limited to the following, a fluorophenyl group, a chlorophenyl group, and a 1,2,3,4,5-pentafluorophenyl group. Examples of the aralkyl group include, but are not limited to the following, a benzyl group and a phenethyl group.

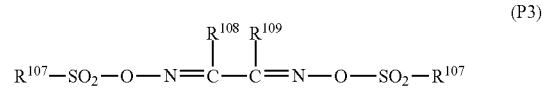
(P3)

In the formula (P3), each of $R^{107}$, $R^{108}$ and $R^{109}$ independently represents a linear, branched or cyclic alkyl group or halogenated alkyl group having 1 to 12 carbon atoms; an aryl group or halogenated aryl group having 6 to 20 carbon atoms; or an aralkyl group having 7 to 12 carbon atoms. $R^{108}$ and $R^{109}$ may be bonded with each other to form a cyclic structure, and if forming a cyclic structure, each of $R^{108}$ and $R^{109}$ represents a linear or branched alkylene group having 1 to 6 carbon atoms.

The alkyl group, halogenated alkyl group, aryl group, halogenated aryl group, and aralkyl group in each of $R^{107}$, $R^{108}$ and $R^{109}$ include the same as those described in $R^{105}$ and $R^{106}$. Herein, examples of the alkylene group in each of $R^{108}$ and $R^{109}$ include, but are not limited to the following, a methylene group, an ethylene group, a propylene group, a butylene group, and a hexylene group.

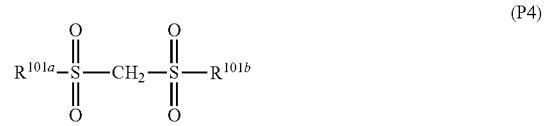
(P4)

In the formula (P4), $R^{101a}$ and $R^{101b}$ are the same as those described above.

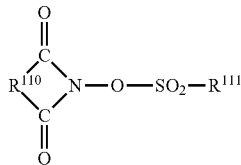

(P5)

In the formula (P5), $R^{110}$ represents an arylene group having 6 to 10 carbon atoms, an alkylene group having 1 to 6 carbon atoms, or an alkenylene group having 2 to 6 carbon atoms, and a part or all of hydrogen atoms of these groups may be further substituted with a linear or branched alkyl group or alkoxy group having 1 to 4 carbon atoms, a nitro group, an acetyl group, or a phenyl group. $R^{111}$ represents a linear, branched or substituted alkyl group, alkenyl group or alkoxyalkyl group having 1 to 8 carbon atoms, a phenyl group, or a naphthyl group, and a part or all of hydrogen atoms of these groups may be further substituted with an alkyl group or alkoxy group having 1 to 4 carbon atoms; a phenyl group that may be substituted with an alkyl group or alkoxy group having 1 to 4 carbon atoms, a nitro group, or an acetyl group; a heteroaromatic group having 3 to 5 carbon atoms; or a chlorine atom or a fluorine atom.

Herein, examples of the arylene group in $R^{110}$ include, but are not limited to the following, a 1,2-phenylene group and a 1,8-naphthylene group. Examples of the alkylene group include, but are not limited to the following, a methylene group, an ethylene group, a trimethylene group, a tetramethylene group, a phenylethylene group, and a norbornane-2,3-diyl group. Examples of the alkenylene group include, but are not limited to the following, a 1,2-vinylene group, a 1-phenyl-1,2-vinylene group, and a 5-norbornene-2,3-diyl group. The alkyl group in $R^{111}$ includes the same as those in $R^{101a}$ to $R^{101c}$. Examples of the alkenyl group include, but are not limited to the following, a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. Examples of the alkoxyalkyl group include, but are not limited to the following, a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Herein, Examples of the alkyl group having 1 to 4 carbon atoms, which may be further substituted, include, but are not limited to the following, a methyl group, an ethyl group, a propyl group, an isopropyl group, a n-butyl group, a an isobutyl group, and a tert-butyl group. Examples of the alkoxy group having 1 to 4 carbon atoms include, but are not limited to the following, a methoxy group, an ethoxy group, a propoxy group, an isopropoxy group, a n-butoxy group, an isobutoxy group, and tert-butoxy group. Examples of the phenyl group that may be substituted with an alkyl group or alkoxy group having 1 to 4 carbon atoms, a nitro group, or an acetyl group include, but are not limited to the following, a phenyl group, a tolyl group, a p-tert-butoxyphenyl group, a p-acetylphenyl group, and a p-nitrophenyl group. Examples of the heteroaromatic group having 3 to 5 carbon atoms include, but are not limited to the following, a pyridyl group and a furyl group.

Specific examples of the acid generator include, but are not limited to the following, onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis[methyl(2-oxocyclopentyl)sulfonium trifluoromethanesulfonate], and 1,2'-naphthylcarbonylmethyltetrahydrothiophenium triflate; diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane; glyoxime derivatives such as bis-(p-toluenesulfonyl)-α-dimethylglyoxime, bis-(p-toluesulfonyl)-α-diphenylglyoxime, bis-(p-toluenesulfonyl)-α-dicyclohexylglyoxime, bis-(p-toluenesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α-dicyclohexylglyoxime, bis-(n-butanesulfonyl)-2,3- pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α-dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α-dimethylglyoxime, bis-(cyclohexanesulfonyl)-α-dimethylglyoxime, bis-(benzenesulfonyl)-α-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime; bissulfone derivatives, such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane; β-ketosulfone derivatives such as 2-cyclohexylcarbonyl-2-(p-toluenesulfonyl)propane and 2-isopropylcarbonyl-2-(p-toluenesulfonyl)propane; disulfone derivatives such as a diphenyldisulfone derivative and a dicyclohexyldisulfone derivative, nitrobenzylsulfonate derivatives such as 2,6-dinitrobenzyl p-toluenesulfonate and 2,4-dinitrobenzyl p-toluenesulfonate; sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid ester derivatives of a N-hydroxyimide compound, such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboxyimide methanesulfonic acid ester, N-hydroxy-5-norbornene-2,3-dicarboxyimide trifluoromethanesulfonic acid ester, and N-hydroxy-5-norbornene-2,3-dicarboxyimide p-toluenesulfonic acid ester.

Among them, in particular, onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-(p-toluenesulfonyl)-α-dimethylglyoxime and bis-(n-butanesulfonyl)-α-dimethylglyoxime, bissulfone derivatives such as bisnaphthylsulfonylmethane; and sulfonic acid ester derivatives of an N-hydroxyimide compound, such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester, and the like are preferably used.

In the material for forming an underlayer film for lithography according to the present embodiment, the content of the acid generator is not particularly limited, but the content is preferably 0.1 to 50 parts by mass and more preferably 0.5 to 40 parts by mass, based on 100 parts by mass of the compound represented by the formula (1) and/or the resin obtained by using the compound as a monomer. The content is set within the above range to result in a tendency to increase the acid generation amount to promote a crosslinking reaction, and also to result in a tendency to suppress the occurrence of the mixing phenomenon with a resist layer.

Furthermore, the material for forming an underlayer film for lithography of the present embodiment may contain a basic compound from the viewpoint of improving preservation stability.

The basic compound serves as a quencher to an acid for preventing a trace amount of the acid generated from the acid generator from promoting a crosslinking reaction. Examples of such a basic compound include primary, secondary, and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and an imide derivative, but are not limited thereto.

Specifically, specific examples of the primary aliphatic amines include, but are not limited to the following, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include, but are not limited to the following, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include, but are not limited to the following, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include, but are not limited to the following, dimethylethylamine, methylethylpropylamine, benzylamine, phenethylamine, and benzyldimethylamine. Specific examples of the aromatic amines and heterocyclic amines include, but are not limited to the following, aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, and N-methylpyrrole), oxazole derivatives (for example, oxazole and isoxazole), thiazole derivatives (for example, thiazole and isothiazole), imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline, 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Furthermore, specific examples of the nitrogen-containing compound having a carboxy group include, but are not limited to the following, aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compound having a sulfonyl group include, but are not limited to the following, 3-pyridinesulfonic acid and pyridinium p-toluenesulfonate. Specific examples of the nitrogen-containing compound having a hydroxyl group, the nitrogen-containing compound having a hydroxyphenyl group, and the alcoholic nitrogen-containing compound include, but are not limited to the following, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Specific examples of the amide derivative include, but are not limited to the following, formamide, N-methylformamide, N,N-dimethylformamide, acetamide, N-methylacetamide, N,N-dimethylacetamide, propionamide, and benzamide. Specific examples of the imide derivative include, but are not limited to the following, phthalimide, succinimide, and maleimide.

In the material for forming an underlayer film for lithography according to the present embodiment, the content of the basic compound is not particularly limited, but the content is preferably 0.001 to 2 parts by mass and more preferably 0.01 to 1 part by mass, based on 100 parts by mass of the compound represented by the formula (1) and the resin obtained by using the compound as a monomer. The content is set within the above preferable range to result in a tendency to improve preservation stability without excessively interrupting a crosslinking reaction.

In addition, the material for forming an underlayer film for lithography of the present embodiment may contain other resins and/or compounds for the purpose of imparting heat curability and controlling absorbance. Such other resins and/or compounds include naphthol resins, xylene resins, naphthol-modified resins, phenol-modified resins of naphthalene resins, polyhydroxystyrene, dicyclopentadiene resins, (meth)acrylate, dimethacrylate, trimethacrylate, tetramethacrylate, resins having a naphthalene ring such as vinylnaphthalene and polyacenaphthylene, resins having a biphenyl ring such as phenanthrenequinone and fluorene, resins having a heterocyclic ring having a hetero atom such as thiophene and indene, and resins not containing an aromatic ring; rosin-based resins, and resins or compounds including an alicyclic structure, such as cyclodextrin, adamantane(poly)ol, tricyclodecane(poly)ol and derivatives thereof, but are not limited thereto. Furthermore, the material for forming an underlayer film for lithography of the present embodiment can also contain a known additive. Examples of the known additive includes, but not limited to the following, an ultraviolet absorber, a surfactant, a colorant and a non-ionic surfactant.

[Underlayer Film for Lithography and Forming Method of Pattern]

An underlayer film for lithography of the present embodiment is formed from the material for forming an underlayer film for lithography of the present embodiment.

In addition, a resist pattern forming method of the present embodiment includes step (A-1) of forming an underlayer film on a substrate by using the material for forming an underlayer film for lithography of the present embodiment, step (A-2) of forming at least one photoresist layer on the underlayer film, and step (A-3) of, after the second forming step, irradiating a predetermined region of the photoresist layer with radiation, followed by developing with an alkali.

Furthermore, a circuit pattern forming method of the present embodiment includes step (B-1) of forming an underlayer film on a substrate by using the material for forming an underlayer film for lithography of the present embodiment, step (B-2) of forming an intermediate layer film on the underlayer film by using a silicon atom-containing resist intermediate layer film material, step (B-3) of forming at least one photoresist layer on the intermediate layer film, step (B-4) of, after step (B-3), irradiating a predetermined region of the photoresist layer with radiation, followed by developing with an alkali to form a resist pattern, and step (B-5) of, after step (B-4), etching the intermediate layer film with the resist pattern as a mask, etching the underlayer film with the obtained intermediate layer film pattern as an etching mask and etching the substrate with the obtained underlayer film pattern as an etching mask, to form a pattern on the substrate.

The underlayer film for lithography of the present embodiment is not particularly limited in terms of the forming method thereof as long as it is formed from the material for forming an underlayer film for lithography of the present embodiment, and a known method can be applied. For example, the underlayer film can be formed by applying the material for forming an underlayer film for lithography of the present embodiment on the substrate by a known coating method or printing method such as spin coating or screen printing, and removing an organic solvent by volatilization or the like.

The underlayer film is preferably baked upon forming in order to suppress the occurrence of the mixing phenomenon with an upperlayer resist and also promote a crosslinking reaction. In this case, the baking temperature is not particularly limited, but it is preferably within the range of 80 to 450° C., and more preferably 200 to 400° C. In addition, the baking time is not also particularly limited, but is preferably within the range of 10 to 300 seconds. Herein, the thickness of the underlayer film can be appropriately selected depending on the required properties, and is not particularly limited, but the thickness is usually preferably about 30 to 20,000 nm and more preferably 50 to 15,000 nm.

After the underlayer film is prepared, in the case of a two-layer process, a silicon-containing resist layer or a usual single-layer resist including a hydrocarbon is preferably prepared on the underlayer film, and in the case of a three-layer process, a silicon-containing intermediate layer is preferably prepared on the underlayer film, and a single-layer resist layer not containing silicon is preferably prepared on the silicon-containing intermediate layer. In these cases, known photoresist materials for forming the resist layer can be used.

After the underlayer film is prepared on the substrate, in the case of a two-layer process, a silicon-containing resist layer or a usual single-layer resist including a hydrocarbon can be prepared on the underlayer film. In the case of a three-layer process, a silicon-containing intermediate layer can be prepared on the underlayer film, and a single-layer resist layer not containing silicon can be prepared on the silicon-containing intermediate layer. In these cases, a photoresist material for forming the resist layer, which can be used, is appropriately selected from known ones, and is not particularly limited.

As the silicon-containing resist material for a two-layer process, a positive-type photoresist material, which contains a silicon atom-containing polymer such as a polysilsesquioxane derivative or a vinylsilane derivative, is preferably used as a base polymer from the viewpoint of oxygen gas-etching resistance. Also, an organic solvent, an acid generator and if necessary a basic compound can be preferably used. Herein, as the silicon atom-containing polymer, a known polymer used in such a resist material can be used.

As the silicon-containing intermediate layer for a three-layer process, a polysilsesquioxane-based intermediate layer is preferably used. The intermediate layer is allowed to have an effect as an antireflective film, and thus tends to make it possible to effectively suppress reflection. For example, if a material including many aromatic groups and having a high substrate-etching resistance is used for the underlayer film in a 193 nm exposure process, a k-value tends to be increased to increase substrate reflection, but the reflection can be suppressed by the intermediate layer to thereby make the substrate reflection 0.5% or less. For the intermediate layer having such an antireflection effect, but not limited to the following, polysilsesquioxane into which a phenyl group or a light-absorbing group having a silicon-silicon bond for 193 nm exposure is introduced and which is to be crosslinked with an acid or heat is preferably used.

An intermediate layer formed by the Chemical Vapour Deposition (CVD) method can also be used. As the intermediate layer having a high effect as an antireflective film, prepared by the CVD method, but not limited to the following, for example, a SiON film is known. In general, the intermediate layer is formed by a wet process such as a spin coating method or screen printing rather than the CVD method in terms of simplicity and cost effectiveness. Herein, the upperlayer resist in a three-layer process may be of positive-type or negative-type, and the same one as a commonly used single-layer resist can be used therefor.

Furthermore, the underlayer film of the present embodiment can also be used as a usual antireflective film for use in a single-layer resist or a usual underlying material for suppressing pattern collapse. The underlayer film of the present embodiment can also be expected to serve as a hard mask for underlying processing because of being excellent in etching resistance for underlying processing.

In the case where a resist layer is formed by the photoresist material, a wet process such as a spin coating method or screen printing is preferably used as in the case of forming the underlayer film. The resist material is coated by a spin coating method or the like and then usually pre-baked, and such pre-baking is preferably performed in the range of 80 to 180° C. for 10 to 300 seconds. Thereafter, in accordance with an ordinary method, the resultant can be subjected to exposure, post-exposure bake (PEB), and development to obtain a resist pattern. Herein, the thickness of the resist film is not particularly limited, but generally, it is preferably 30 to 500 nm and more preferably 50 to 400 nm.

Light for use in exposure may be appropriately selected depending on the photoresist material to be used. In general, examples thereof include high energy radiation having a wavelength of 300 nm or less, specifically, excimer lasers of 248 nm, 193 nm, and 157 nm, a soft X-ray of 3 to 20 nm, electron beam, and an X-ray.

The resist pattern formed by the above method is a pattern whose collapse is suppressed by the underlayer film of the present embodiment. Therefore, the underlayer film of the present embodiment can be used to thereby obtain a finer pattern, and an exposure amount necessary for obtaining such a resist pattern can be reduced.

Then, the obtained resist pattern is used as a mask to perform etching. As the etching of the underlayer film in a two-layer process, gas etching is preferably used. As the gas etching, etching using oxygen gas is suitable. In addition to oxygen gas, an inert gas such as He and Ar, and CO, $CO_2$, $NH_3$, $SO_2$, $N_2$, $NO_2$, and $H_2$ gases can also be added. The gas etching can also be performed not using oxygen gas but using only CO, $CO_2$, $NH_3$, $N_2$, $NO_2$, and $H_2$ gases. In particular, the latter gases are preferably used for protecting a side wall for preventing a pattern side wall from being undercut.

On the other hand, also in the etching of the intermediate layer in a three-layer process, gas etching is preferably used. As the gas etching, the same one as the one described in a two-layer process can be applied. In particular, the intermediate layer is preferably processed in a three-layer process using a fluorocarbon gas with the resist pattern as a mask. Thereafter, as described above, the intermediate layer pattern is used as a mask to perform, for example, oxygen gas etching, thereby processing the underlayer film.

Herein, in the case where an inorganic hard mask intermediate layer film is formed as the intermediate layer, a silicon oxide film, a silicon nitride film, and a silicon oxynitride film (SiON film) are formed by the CVD method, the ALD method, and the like. The nitride film forming method that can be used is, but not limited to the following, any method described in, for example, Japanese Patent Laid-Open No. 2002-334869 (Patent Literature 6) and WO2004/066377 (Patent Literature 7). While the photoresist film can be directly formed on such an intermediate layer film, an organic antireflective film (BARC) may also be formed on the intermediate layer film by spin coating, and the photoresist film may also be formed thereon.

As the intermediate layer, a polysilsesquioxane-based intermediate layer is also preferably used. The resist intermediate layer film is allowed to have an effect as an antireflective film, and thus tends to make it possible to effectively suppress reflection. A specific material for the polysilsesquioxane-based intermediate layer that can be used is, but not limited to the following, any material described in, for example, Japanese Patent Laid-Open No. 2007-226170 (Patent Literature 8) and Japanese Patent Laid-Open No. 2007-226204 (Patent Literature 9).

The next etching of the substrate can also be performed by an ordinary method, and, for example, when the substrate is made of $SiO_2$ or SiN, etching with mainly a fluorocarbon gas can be performed, and when the substrate is made of p-Si, Al, or W, etching mainly using a chlorine-based gas or bromine-based gas can be performed. In the case where the substrate is processed by the etching with a fluorocarbon gas, the silicon-containing resist in a two-layer resist process and the silicon-containing intermediate layer in a three-layer process are peeled off at the same time as the processing of the substrate. On the other hand, in the case where the substrate is processed by the etching with a chlorine-based gas or bromine-based gas, the silicon-containing resist layer or the silicon-containing intermediate layer is peeled off separately, and is generally peeled off by dry etching with a fluorocarbon gas after the substrate is processed.

The underlayer film of the present embodiment is characterized by being excellent in etching resistance of such a substrate. Herein, the substrate that can be used is appropriately selected from known ones, and is not particularly limited, but includes Si, α-Si, p-Si, $SiO_2$, SiN, SiON, W, TiN, and Al substrates. In addition, the substrate may also be a laminate having a processed film (processed substrate) on a base material (support). Such a processed film includes various Low-k films made of Si, $SiO_2$, SiON, SiN, p-Si, α-Si, W, W—Si, Al, Cu, and Al—Si, and stopper films thereof, and a material different from the base material (support) is usually used therefor. Herein, the thickness of the substrate to be processed or the processed film is not particularly limited, but it is usually preferably about 50 to 10,000 nm and more preferably 75 to 5,000 nm.

[Method for Purifying Compound or Resin]

A method for purifying the compound or the resin of the present embodiment includes a step of bringing a solution (hereinafter, also referred to as "solution (A)") including an organic solvent optionally immiscible with water, and the compound or the resin into contact with an acidic aqueous solution for extraction. More specifically, in the present embodiment, the compound represented by the formula (1) or the resin obtained by using the compound as a monomer can be purified by dissolving the compound or the resin in an organic solvent optionally immiscible with water, bringing the solution into contact with an acidic aqueous solution for performing an extraction treatment, to thereby transfer a metal content included in the solution (A) including the compound or the resin and the organic solvent to an aqueous phase, and then separating an organic phase and the aqueous phase. The method of the present embodiment can allow the contents of various metals in the compound represented by the formula (1) or the resin obtained by using the compound as a monomer to be remarkably reduced.

In the present embodiment, the organic solvent optionally immiscible with water means an organic solvent whose solubility in water at room temperature is less than 30%. Herein, the solubility is preferably less than 20%, more preferably less than 10%. The organic solvent optionally immiscible with water is not particularly limited, but it is preferably an organic solvent that can be safely applied to a semiconductor manufacturing process. The amount of the organic solvent to be used is usually about 1 to 100 times the amount of the compound represented by the formula (1) or the resin obtained by using the compound as a monomer, to be used.

Specific examples of the solvent to be used include, but not limited to the following, ethers such as diethyl ether and diisopropyl ether, esters such as ethyl acetate, n-butyl acetate and isoamyl acetate, ketones such as methyl ethyl ketone, methyl isobutyl ketone, ethyl isobutyl ketone, cyclohexanone, cyclopentanone, 2-heptanone and 2-pentanone, glycol ether acetates such as ethylene glycol monoethyl ether acetate, ethylene glycol monobutyl ether acetate, propylene glycol monomethyl ether acetate (PGMEA) and propylene glycol monoethyl ether acetate, aliphatic hydrocarbons such as n-hexane and n-heptane, aromatic hydrocarbons such as toluene and xylene, and halogenated hydrocarbons such as methylene chloride and chloroform. Among them, toluene, 2-heptanone, cyclohexanone, cyclopentanone, methyl isobutyl ketone, propylene glycol monomethyl ether acetate, ethyl acetate, and the like are preferable, and cyclohexanone and propylene glycol monomethyl ether acetate are more preferable. These solvents can be used singly or as a mixture of two or more thereof.

The acidic aqueous solution to be used in the present embodiment is appropriately selected from aqueous solutions in which an organic or inorganic compound commonly known is dissolved in water. Examples include an aqueous solution in which a mineral acid such as hydrochloric acid, sulfuric acid, nitric acid or phosphoric acid is dissolved in water, or an aqueous solution in which an organic acid such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid or trifluoroacetic acid is dissolved in water. These acidic aqueous solutions can be used singly or in combinations of two or more thereof. Among these acidic aqueous solutions, an aqueous solution of sulfuric acid, nitric acid, or a carboxylic acid such as acetic acid, oxalic acid, tartaric acid or citric acid is preferable, an aqueous solution of sulfuric acid, oxalic acid, tartaric acid or citric acid is more preferable, and an aqueous solution of oxalic acid is further preferable. It is considered that a polyvalent carboxylic acid such as oxalic acid, tartaric acid and citric acid is coordinated with a metal ion to exert a chelating effect, and therefore tends to allow a metal to be more effectively removed. In addition, the water to be here used is preferably water having a low metal content according to the purpose of the present embodiment, such as ion-exchange water.

The pH of the acidic aqueous solution to be used in the present embodiment is not particularly limited, but the acidity of the aqueous solution is preferably adjusted in consideration of the effect on the compound represented by the formula (1) or the resin obtained by using the compound as a monomer. The pH is usually in the range from about 0 to 5, preferably about 0 to 3.

The amount of the acidic aqueous solution to be used in the present embodiment is not particularly limited, but the amount to be used is preferably adjusted from the viewpoint of reducing the number of extractions for metal removal and the viewpoint of ensuring operation property in consideration of the total amount of the liquid. The amount of the aqueous solution to be used is usually 10 to 200% by mass, preferably 20 to 100% by mass, relative to the solution of the compound represented by the formula (1) or the resin obtained by using the compound as a monomer, dissolved in the organic solvent.

In the present embodiment, the acidic aqueous solution can be brought into contact with the solution (A) including the compound represented by the formula (1) or the resin obtained by using the compound as a monomer and the organic solvent optionally immiscible with water, to thereby extract the metal content.

The temperature in performing of the extraction treatment is usually in the range from 20 to 90° C., preferably 30 to 80° C. The extraction operation is performed by, for example, well mixing with stirring or the like and thereafter standing. Thus, the metal content included in the solution including the compound represented by the formula (1) or the resin obtained by using the compound as a monomer and the organic solvent is transferred to the aqueous phase. In addition, the operation can allow the acidity of the solution to be reduced, suppressing the change of properties of the compound represented by the formula (1) or the resin obtained by using the compound as a monomer.

The resulting mixture is separated to the solution phase including the compound represented by the formula (1) or the resin obtained by using the compound as a monomer and the organic solvent, and the aqueous phase, and therefore the solution including the compound represented by the formula (1) or the resin obtained by using the compound as a monomer and the organic solvent is recovered by decantation or the like. The standing time is not particularly limited, but the standing time is preferably adjusted from the viewpoint of providing better separation to the solution phase including the organic solvent, and the aqueous phase. The standing time is usually 1 minute or more, preferably 10 minutes or more, more preferably 30 minutes or more. In addition, the extraction treatment may be performed only once, but is also effectively performed with operations such as mixing, standing and separation being repeatedly performed multiple times.

In the present embodiment, a step of performing an extraction treatment with water is preferably further included after the step of bringing the solution (A) into contact with the acidic aqueous solution for extraction. That is, preferably, the extraction treatment is performed by using the acidic aqueous solution, thereafter the solution (A) including the compound represented by the formula (1) or the resin obtained by using the compound as a monomer, extracted and recovered from the aqueous solution, and the organic solvent, is preferably further subjected to the extraction treatment with water. The extraction treatment with water is performed by, for example, well mixing with stirring or the like and thereafter standing. The resulting solution is separated to the solution phase including the compound represented by the formula (1) or the resin obtained by using the compound as a monomer and the organic solvent, and the aqueous phase, and therefore the solution phase including the compound represented by the formula (1) or the resin obtained by using the compound as a monomer and the organic solvent is recovered by decantation or the like. In addition, the water to be here used is preferably water having a low metal content according to the purpose of the present embodiment, such as ion-exchange water. The extraction treatment may be performed only once, but is also effectively performed with operations such as mixing, standing and separation being repeatedly performed multiple times. In addition, conditions in the extraction treatment, such as the ratio of both to be used, the temperature and the time, are not particularly limited, but may be the same as in the case of the contact treatment with the acidic aqueous solution above.

The water content that can be incorporated in the solution thus obtained, including the compound represented by the formula (1) or the resin obtained by using the compound as a monomer and the organic solvent, can be easily removed by performing an operation such as distillation under reduced pressure. In addition, an organic solvent can be if necessary added to adjust the concentration of the compound represented by the formula (1) or the resin obtained by using the compound as a monomer to any concentration.

The method of isolating the compound represented by the formula (1) or the resin obtained by using the compound as a monomer from the resulting solution including the compound represented by the formula (1) or the resin obtained by using the compound as a monomer and the organic solvent can be performed by a known method such as removal under reduced pressure, separation by reprecipitation and a combination thereof. If necessary, a known treatment such as a concentration operation, a filtration operation, a centrifugation operation and a drying operation can be performed.

EXAMPLES

Hereinafter, the present embodiment will be described by Synthesis Examples and Examples in more detail, but the present embodiment is not limited thereto at all.

(Carbon Concentration and Oxygen Concentration)

The carbon concentration and the oxygen concentration (% by mass) were measured by organic element analysis.

Apparatus: CHN CORDER MT-6 (manufactured by Yanaco Bunseki Kogyo Co.)

(Molecular Weight)

Measurement was performed by LC-MS analysis using Acquity UPLC/MALDI-Synapt HDMS manufactured by Water.

(Molecular Weight in Terms of Polystyrene)

Gel permeation chromatography (GPC) analysis was used to determine the weight average molecular weight (Mw) and the number average molecular weight (Mn) in terms of polystyrene, and to determine the degree of dispersion (Mw/Mn).

Apparatus: Shodex GPC-101 type (manufactured by Showa Denko K. K.)

Column: KF-80M×3

Eluent: THF 1 mL/min

Temperature: 40° C.

(Pyrolysis Temperature (Tg))

An EXSTAR 6000 DSC apparatus manufactured by SII NanoTechnology Inc. was used, and about 5 mg of a sample was placed in an unsealed aluminum container and heated to 500° C. at a rate of temperature rise of 10° C./min in a nitrogen gas (30 mL/min) stream. In this time, a temperature at which a reducing portion appeared on the base line was defined as a pyrolysis temperature (Tg).

(Solubility)

The amount of each compound dissolved in 1-methoxy-2-propanol (PGME) and propylene glycol monomethyl ether acetate (PGMEA) was measured at 23° C., and the results were evaluated according to the following criteria.

Evaluation A: 20% by weight or more

Evaluation B: 10% by weight or more and less than 20% by weight

Evaluation C: less than 10% by weight

Example 1

Synthesis of BiF-1

A container having an inner volume of 200 mL, equipped with a stirrer, a condenser and a burette, was prepared. To this container were charged 30 g (161 mmol) of 4,4-biphenol (reagent produced by Tokyo Chemical Industry Co., Ltd.), 15 g (82 mmol) of 4-biphenylaldehyde (produced by Mitsubishi Gas Chemical Company, Inc.) and 100 mL of butyl acetate, and 3.9 g (21 mmol) of p-toluenesulfonic acid (reagent produced by Kanto Chemical Co., Inc.) was added thereto to prepare a reaction liquid. The reaction liquid was stirred at 90° C. for 3 hours to perform a reaction. Then, the reaction liquid was concentrated, 50 g of heptane was added thereto to precipitate a reaction product, and the resultant was cooled to room temperature followed by filtration for separation. A solid obtained by filtration was dried, and thereafter separated and purified by column chromatography to thereby provide 5.8 g of an objective compound (BiF-1) represented by the following formula.

Herein, the following peaks were observed by 400 MHz-$^1$H-NMR, and it was confirmed that the compound had a chemical structure of the following formula.

$^1$H-NMR: (d-DMSO, internal standard TMS)

δ (ppm) 9.4 (4H, O—H), 6.8-7.8 (22H, Ph-H), 6.2 (1H, C—H)

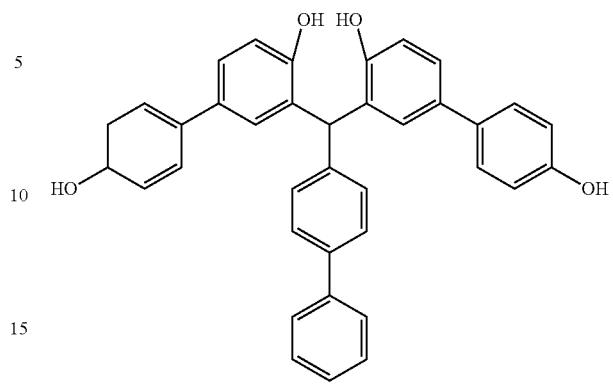

(BiF-1)

As a result of organic element analysis, the carbon concentration and the oxygen concentration of the resulting compound (BiF-1) were determined to be 82.9% and 11.8%, respectively. The carbon content rate was high and the oxygen content rate was low, and it was thus evaluated that compound (BiF-1) had a high etching resistance.

The molecular weight of the resulting compound was measured by the above method, and as a result, it was determined to be 536.

As a result of thermogravimetric measurement (TG), the 10% thermal weight loss temperature of the resulting compound (BiF-1) was determined to be 400° C. or higher. Therefore, the compound was evaluated to have a high heat resistance and be applicable to high-temperature baking.

As a result of evaluation of the solubility in PGME and PGMEA, the solubility was determined to be 30% by weight or more (Evaluation A) and compound (BiF-1) was evaluated to have an excellent solubility. Therefore, compound (BiF-1) was evaluated to have a high storage stability in a solution state and also be sufficiently applicable to an edge bead rinse liquid (mixed liquid of PGME/PGMEA) widely used in a semiconductor microfabrication process.

Example 2

Synthesis of BiF-2

A container having an inner volume of 300 mL, equipped with a stirrer, a condenser and a burette, was prepared. To this container were charged 60 g (178 mmol) of OPP-BP (produced by Honshu Chemical Industry Co., Ltd.), 16 g (89 mmol) of 4-biphenylaldehyde (produced by Mitsubishi Gas Chemical Company, Inc.) and 100 mL of butyl acetate, and 3.9 g (21 mmol) of p-toluenesulfonic acid (reagent produced by Kanto Chemical Co., Inc.) was added thereto to prepare a reaction liquid. The reaction liquid was stirred at 90° C. for 5 hours to perform a reaction. Then, the reaction liquid was concentrated, 100 g of heptane was added thereto to precipitate a reaction product, and the resultant was cooled to room temperature followed by filtration for separation. A solid obtained by filtration was dried, and thereafter separated and purified by column chromatography to thereby provide 7.5 g of an objective compound (BiF-2) represented by the following formula.

Herein, the following peaks were observed by 400 MHz-$^1$H-NMR, and it was confirmed that the compound had a chemical structure of the following formula.

$^1$H-NMR: (d-DMSO, internal standard TMS)

δ (ppm) 9.1 (4H, O—H), 6.8-8.2 (39H, Ph-H), 6.5 (1H, C—H)

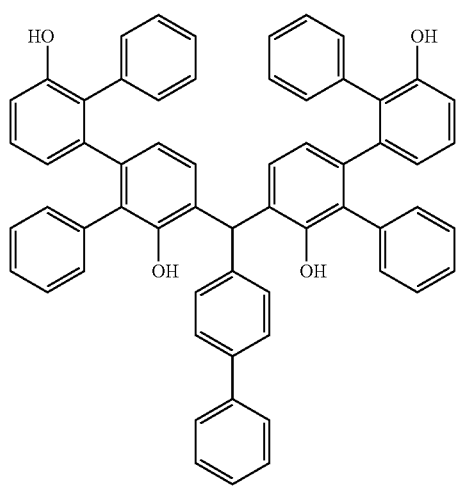

(BiF-2)

As a result of organic element analysis, the carbon concentration and the oxygen concentration of the resulting compound (BiF-2) were determined to be 87.1% and 7.6%, respectively. The carbon content rate was high and the oxygen content rate was low, and it was thus evaluated that compound (BiF-2) had a high etching resistance.

The molecular weight of the resulting compound was measured by the above method, and as a result, it was determined to be 840.

As a result of thermogravimetric measurement (TG), the 10% thermal weight loss temperature of the resulting compound (BiF-2) was determined to be 400° C. or higher. Therefore, the compound was evaluated to have a high heat resistance and be applicable to high-temperature baking.

As a result of evaluation of the solubility in PGME and PGMEA, the solubility was determined to be 30% by weight or more (Evaluation A) and compound (BiF-2) was evaluated to have an excellent solubility. Therefore, compound (BiF-2) was evaluated to have a high storage stability in a solution state and also be sufficiently applicable to an edge bead rinse liquid (mixed liquid of PGME/PGMEA) widely used in a semiconductor microfabrication process.

Example 3

A four-neck flask having a bottom outlet and an inner volume of 1 L, equipped with a Dimroth condenser, a thermometer and a stirring blade was prepared. To this four-neck flask were charged 376 g (0.7 mol) of compound (BiF-1) obtained in Example 1, 210 g (2.8 mol as formaldehyde, produced by Mitsubishi Gas Chemical Company, Inc.) of a 40% by mass aqueous formalin solution and 0.01 mL of 98% by mass sulfuric acid under a nitrogen stream, and the reaction was allowed to run under ordinary pressure for 7 hours with refluxing at 100° C. Thereafter, 180 g of ethylglyme (special grade chemical, produced by Tokyo Chemical Industry Co., Ltd.) as a dilution solvent was added to the reaction liquid and left to stand, and then an aqueous phase being a bottom phase was removed. Furthermore, the resultant was neutralized and washed with water, and the solvent was distilled off under reduced pressure to thereby provide 354 g of resin (BiFP-1) as a light-brown solid.

The molecular weight in terms of polystyrene with respect to the resulting resin (BiFP-1) was measured by the above method, and as a result, Mn was determined to be 1211, Mw was determined to be 2167 and Mw/Mn was determined to be 1.79.

As a result of organic element analysis, the carbon concentration and the oxygen concentration of the resulting resin (BiFP-1) were determined to be 81.2% and 7.6%, respectively. The carbon content rate was high, the aromatic ring ratio was high and the oxygen content rate was low, and it was thus evaluated that resin (BiFP-1) had a high etching resistance.

As a result of thermogravimetric measurement (TG), the 10% thermal weight loss temperature of resin (BiFP-1) was determined to be 400° C. or higher. Therefore, the resin was evaluated to have a high heat resistance and be applicable to high-temperature baking.

As a result of evaluation of the solubility in PGME and PGMEA, the solubility was determined to be 30% by weight or more (Evaluation A), and resin (BiFP-1) was evaluated to have an excellent solubility. Therefore, resin (BiFP-1) was evaluated to have a high storage stability in a solution state and also be sufficiently applicable to an edge bead rinse liquid (mixed liquid of PGME/PGMEA) widely used in a semiconductor microfabrication process.

Example 4

A four-neck flask having a bottom outlet and an inner volume of 1 L, equipped with a Dimroth condenser, a thermometer and a stirring blade was prepared. To this four-neck flask were charged 134 g (0.25 mol) of compound (BiF-1) obtained in Example 1, 182 g of 4-biphenylaldehyde (1.0 mol, produced by Mitsubishi Gas Chemical Company, Inc.) and 0.5 g of paratoluenesulfonic acid under a nitrogen stream, 180 g of ethylglyme (special grade chemical, produced by Tokyo Chemical Industry Co., Ltd.) as a solvent was added thereto, and the reaction was allowed to run under ordinary pressure at 120° C. for 7 hours. Thereafter, 180 g of ethylglyme (special grade chemical, produced by Tokyo Chemical Industry Co., Ltd.) as a dilution solvent was added to the reaction liquid and left to stand, and then an aqueous phase being a bottom phase was removed. Furthermore, the reaction liquid neutralized and washed with water was dropped in 600 g of a poor solvent, n-heptane (special grade chemical, produced by Kanto Chemical Co., Inc.) to precipitate a solid. The solvent was removed by drying under reduced pressure to thereby provide 254 g of resin (BiFP-2) as a light-brown solid.

The molecular weight in terms of polystyrene with respect to the resulting resin (BiFP-2) was measured by the above method, and as a result, Mn was determined to be 1345, Mw was determined to be 2461 and Mw/Mn was determined to be 1.83.

As a result of organic element analysis, the carbon concentration and the oxygen concentration of the resulting compound (BiFP-2) were determined to be 83.2% and 4.6%, respectively. The carbon content rate was high and the oxygen content rate was low, and it was thus evaluated that compound (BiFP-2) had a high etching resistance.

As a result of thermogravimetric measurement (TG), the 10% thermal weight loss temperature of the resulting compound (BiFP-2) was determined to be 400° C. or higher. Therefore, the compound was evaluated to have a high heat resistance and be applicable to high-temperature baking.

As a result of evaluation of the solubility in PGME and PGMEA, the solubility was determined to be 30% by weight or more (Evaluation A), and compound (BiFP-2) was evaluated to have an excellent solubility. Therefore, compound (BiFP-2) was evaluated to have a high storage stability in a solution state and also be sufficiently applicable to an edge bead rinse liquid (mixed liquid of PGME/PGMEA) widely used in a semiconductor microfabrication process.

Example 5

Synthesis of TeF-1

A container having an inner volume of 500 mL, equipped with a stirrer, a condenser and a burette, was prepared. To this container were charged 30 g (161 mmol) of 4,4-biphenol (reagent produced by Tokyo Chemical Industry Co., Ltd.), 8.5 g (40 mmol) of 4,4'-biphenyldicarboxaldehyde (reagent produced by Tokyo Chemical Industry Co., Ltd.) and 300 g of ethylglyme (special grade chemical, produced by Tokyo Chemical Industry Co., Ltd.), and 3.9 g (21 mmol) of p-toluenesulfonic acid (reagent produced by Kanto Chemical Co., Inc.) was added thereto to prepare a reaction liquid. The reaction liquid was stirred at 90° C. for 3 hours to perform a reaction. Then, the reaction liquid was concentrated, 50 g of heptane was added thereto to precipitate a reaction product, and the resultant was cooled to room temperature followed by filtration for separation. A solid obtained by filtration was dried, and thereafter separated and purified by column chromatography to thereby provide 4.0 g of an objective compound (TeF-1) represented by the following formula.

Herein, the following peaks were observed by 400 MHz-$^1$H-NMR, and it was confirmed that the compound had a chemical structure of the following formula.

$^1$H-NMR: (d-DMSO, internal standard TMS)
δ (ppm) 9.4 (8H, O—H), 6.8-7.8 (36H, Ph-H), 6.2 (2H, C—H)

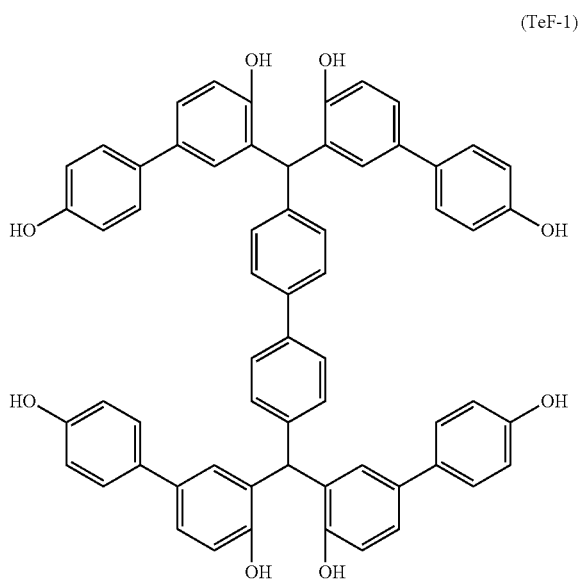 [SMILES: Oc1ccc(-c2ccc(O)c(C(c3ccc(-c4ccc(C(c5cc(-c6ccc(O)cc6)ccc5O)c5cc(-c6ccc(O)cc6)ccc5O)cc4)cc3)c3cc(-c4ccc(O)cc4)ccc3O)c2)cc1]

(TeF-1)

As a result of organic element analysis, the carbon concentration and the oxygen concentration of the resulting compound (TeF-1) were determined to be 81.03% and 13.93%, respectively. The carbon content rate was high and the oxygen content rate was low, and it was thus evaluated that compound (TeF-1) had a high etching resistance.

The molecular weight of the resulting compound was measured by the above method, and as a result, it was determined to be 918.

As a result of thermogravimetric measurement (TG), the 10% thermal weight loss temperature of the resulting compound (TeF-1) was determined to be 400° C. or higher. Therefore, the compound was evaluated to have a high heat resistance and be applicable to high-temperature baking.

As a result of evaluation of the solubility in PGME and PGMEA, the solubility was determined to be 30% by weight or more (Evaluation A) and compound (TeF-1) was evaluated to have an excellent solubility. Therefore, compound (TeF-1) was evaluated to have a high storage stability in a solution state and also be sufficiently applicable to an edge bead rinse liquid (mixed liquid of PGME/PGMEA) widely used in a semiconductor microfabrication process.

Example 6

Synthesis of TeF-2

A container having an inner volume of 500 mL, equipped with a stirrer, a condenser and a burette, was prepared. To this container were charged 30 g (161 mmol) of 4,4-biphenol (reagent produced by Tokyo Chemical Industry Co., Ltd.), 5.4 g (40 mmol) of terephthalaldehyde (reagent produced by Tokyo Chemical Industry Co., Ltd.) and 300 g of ethylglyme (special grade chemical, produced by Tokyo Chemical Industry Co., Ltd.), and 3.9 g (21 mmol) of p-toluenesulfonic acid (reagent produced by Kanto Chemical Co., Inc.) was added thereto to prepare a reaction liquid. The reaction liquid was stirred at 90° C. for 3 hours to perform a reaction. Then, the reaction liquid was concentrated, 50 g of heptane was added thereto to precipitate a reaction product, and the resultant was cooled to room temperature followed by filtration for separation. A solid obtained by filtration was dried, and thereafter separated and purified by column chromatography to thereby provide 3.2 g of an objective compound (TeF-2) represented by the following formula.

Herein, the following peaks were observed by 400 MHz-$^1$H-NMR, and it was confirmed that the compound had a chemical structure of the following formula.

$^1$H-NMR: (d-DMSO, internal standard TMS)
δ (ppm) 9.4 (8H, O—H), 6.8-7.8 (32H, Ph-H), 6.2 (2H, C—H)

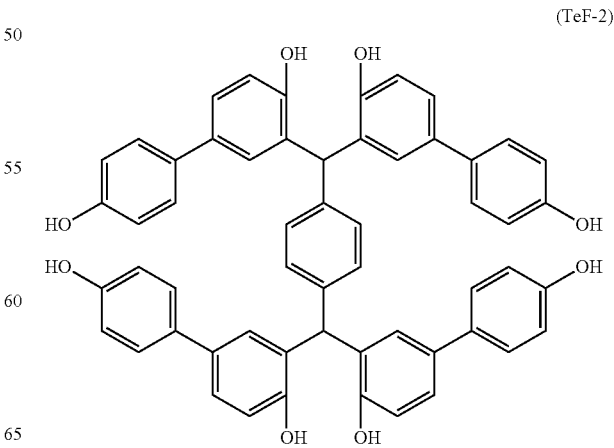

(TeF-2)

As a result of organic element analysis, the carbon concentration and the oxygen concentration of the resulting compound (TeF-2) were determined to be 79.79% and 15.18%, respectively. The carbon content rate was high and the oxygen content rate was low, and it was thus evaluated that compound (TeF-2) had a high etching resistance.

The molecular weight of the resulting compound was measured by the above method, and as a result, it was determined to be 842.

As a result of thermogravimetric measurement (TG), the 10% thermal weight loss temperature of the resulting compound (TeF-2) was determined to be 400° C. or higher. Therefore, the compound was evaluated to have a high heat resistance and be applicable to high-temperature baking.

As a result of evaluation of the solubility in PGME and PGMEA, the solubility was determined to be 30% by weight or more (Evaluation A) and compound (TeF-2) was evaluated to have an excellent solubility. Therefore, compound (TeF-2) was evaluated to have a high storage stability in a solution state and also be sufficiently applicable to an edge bead rinse liquid (mixed liquid of PGME/PGMEA) widely used in a semiconductor microfabrication process.

Comparative Example 1

A four-neck flask having a bottom outlet and an inner volume of 10 L, equipped with a Dimroth condenser, a thermometer and a stirring blade was prepared. To this four-neck flask were charged 1.09 kg (7 mol, produced by Mitsubishi Gas Chemical Company, Inc.) of 1,5-dimethylnaphthalene, 2.1 kg (28 mol as formaldehyde, produced by Mitsubishi Gas Chemical Company, Inc.) of a 40% by mass aqueous formalin solution and 0.97 mL of 98% by mass sulfuric acid (produced by Kanto Chemical Co., Inc.) under a nitrogen stream, and allowed the reaction to run under ordinary pressure for 7 hours with refluxing at 100° C. Thereafter, ethylbenzene (special grade chemical, produced by Wako Pure Chemical Industries, Ltd.) (1.8 kg) as a dilution solvent was added to the reaction solution and left to stand, and then an aqueous phase being a bottom phase was removed. Furthermore, the resultant was neutralized and washed with water, and ethylbenzene and the unreacted 1,5-dimethylnaphthalene were distilled off under reduced pressure, thereby providing 1.25 kg of a dimethylnaphthalene formaldehyde resin as a light-brown solid.

With respect to the molecular weight of the resulting dimethylnaphthalene formaldehyde, Mn was determined to be 562, Mw was determined to be 1168 and Mw/Mn was determined to be 2.08. In addition, the carbon concentration was determined to be 84.2% by mass, and the oxygen concentration was determined to be 8.3% by mass.

Subsequently, a four-neck flask having an inner volume of 0.5 L, equipped with a Dimroth condenser, a thermometer and a stirring blade, was prepared. To this four-neck flask were charged 100 g (0.51 mol) of the dimethylnaphthalene formaldehyde resin obtained as described above and 0.05 g of paratoluenesulfonic acid under a nitrogen stream, heated for 2 hours with the temperature being raised to 190° C., and then stirred. Thereafter, 52.0 g (0.36 mol) of 1-naphthol was further added thereto, and further heated to 220° C. to allow the reaction to run for 2 hours. After being diluted with a solvent, the resultant was neutralized and washed with water, and the solvent was removed under reduced pressure to thereby provide 126.1 g of a modified resin (CR-1) as a blackish brown solid.

With respect to the resulting resin (CR-1), Mn was determined to be 885, Mw was determined to be 2220 and Mw/Mn was determined to be 4.17. In addition, the carbon concentration was determined to be 89.1% by mass and the oxygen concentration was determined to be 4.5% by mass.

As a result of thermogravimetric measurement (TG), the 10% thermal weight loss temperature of the resulting resin (CR-1) was less than 350° C. Therefore, the resin was evaluated to have difficulty in application to high-temperature baking where high etching resistance and heat resistance were required.

As a result of evaluation of the solubility in PGME and PGMEA, the solubility was evaluated to be determined to be 10% by weight or more and less than 20% by weight (Evaluation B).

Examples 7 to 12 and Comparative Example 2

Each material for forming an underlayer film for lithography was prepared so that each composition shown in Table 1 was achieved. That is, the following materials were used.

Acid generator: di-tert-butyldiphenyliodonium nonafluoromethanesulfonate (DTDPI) produced by Midori Kagaku Co., Ltd.

Crosslinking agent: Nikalac MX270 (Nikalac) produced by Sanwa Chemical Co., Ltd.

Organic solvent: propylene glycol monomethyl ether acetate acetate (PGMEA)

Novolac: PSM4357 produced by Gun Ei Chemical Industry Co., Ltd.

Then, each material for forming an underlayer film of Examples 7 to 12 and Comparative Example 2 was spin-coated on a silicon substrate, thereafter baked at 240° C. for 60 seconds and further at 400° C. for 120 seconds to prepare each underlayer film having a film thickness of 200 nm.

An etching test was performed under conditions shown below to evaluate etching resistance. The evaluation results are shown in Table 1.

[Etching Test]

Etching apparatus: RIE-10NR manufactured by Samco Inc.

Output: 50 W
Pressure: 20 Pa
Time: 2 min
Etching gas
Ar gas flow rate: $CF_4$ gas flow rate: $O_2$ gas flow rate=50:5:5 (sccm)

[Evaluation of Etching Resistance]

The evaluation of etching resistance was performed according to the following procedure.

First, an underlayer film of novolac was prepared under the same conditions as those in Examples 7 to 12 except that novolac (PSM4357 produced by Gunei Chemical Industry Co., Ltd.) was used instead of the compounds used in Examples 7 to 12. Then, the etching test was performed with respect to the underlayer film of novolac as a subject, and the etching rate in that time was measured.

Then, the etching test was performed with respect to each underlayer film of Examples 7 to 12 and Comparative Example 2 as a subject, and the etching rate in that time was measured.

Then, the etching resistances were evaluated according to the following criteria based on the etching rate of the underlayer film of novolac.

<Evaluation Criteria>

A; etching rate of less than −10% compared with the underlayer film of novolac

B; etching rate of −10% to +5% compared with underlayer film of novolac

C; etching rate of more than +5% compared with the underlayer film of novolac

TABLE 1

| | Compound or Resin (parts by mass) | Organic solvent (parts by mass) | Acid generator (parts by mass) | Cross-linking agent (parts by mass) | Evaluation of etching resistance |
|---|---|---|---|---|---|
| Example 7 | BiF-1 (10) | PGMEA (90) | DTDPI (0.5) | Nikalac (0.5) | A |
| Example 8 | BiF-2 (10) | PGMEA (90) | DTDPI (0.5) | Nikalac (0.5) | A |
| Example 9 | BiFP-1 (10) | PGMEA (90) | DTDPI (0.5) | Nikalac (0.5) | A |
| Example 10 | BiFP-2 (10) | PGMEA (90) | DTDPI (0.5) | Nikalac (0.5) | A |
| Example 11 | TeF-1 (10) | PGMEA (90) | DTDPI (0.5) | Nikalac (0.5) | A |
| Example 12 | Tef-2 (10) | PGMEA (90) | DTDPI (0.5) | Nikalac (0.5) | A |
| Comparative Example 2 | CR-1 (10) | PGMEA (90) | DTDPI (0.5) | Nikalac (0.5) | C |

Example 13

Then, the solution of the material for forming an underlayer film for lithography in Example 7 was coated on a SiO$_2$ substrate having a film thickness of 300 nm, and baked at 240° C. for 60 seconds and further at 400° C. for 120 seconds to thereby form an underlayer film having a film thickness of 70 nm. A resist solution for ArF was coated on the underlayer film, and baked at 130° C. for 60 seconds to thereby form a photoresist layer having a film thickness of 140 nm.

Herein, as the resist solution for ArF, one prepared by blending 5 parts by mass of the compound of the following formula (11), 1 part by mass of triphenylsulfonium nonafluoromethanesulfonate, 2 parts by mass of tributylamine, and 92 parts by mass of PGMEA was used.

A compound of formula (11) was prepared as follows. That is, 4.15 g of 2-methyl-2-methacryloyloxyadamantane, 3.00 g of methacryloyloxy-γ-butyrolactone, 2.08 g of 3-hydroxy-1-adamantyl methacrylate and 0.38 g of azobisisobutyronitrile were dissolved in 80 mL of tetrahydrofuran to provide a reaction solution. This reaction solution was subjected to polymerization under a nitrogen atmosphere for 22 hours with the reaction temperature being kept at 63° C., and thereafter the reaction solution was dropped in 400 mL of n-hexane. A product resin thus obtained was solidified and purified, and a white powder produced was taken by filtration and dried under reduced pressure at 40° C. overnight to provide a compound represented by the following formula.

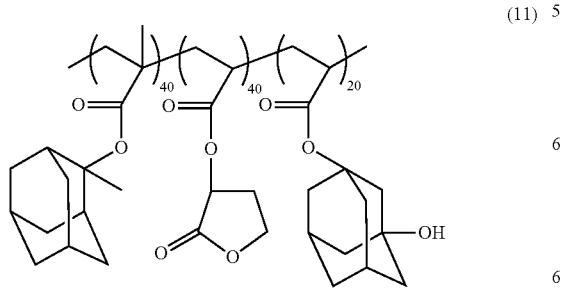

(11)

In the formula (11), the numerals 40, 40, and 20 indicate the proportions of the respective constituent units, and do not mean a block copolymer.

Then, the photoresist layer was exposed by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern.

Comparative Example 3

Except that no underlayer film was formed, the same manner as in Example 13 was performed to form a photoresist layer directly on a SiO$_2$ substrate to provide a positive-type resist pattern.

[Evaluation]

The shapes of the resist patterns of 55 nm L/S (1:1) and 80 nm L/S (1:1) provided in each of Example 13 and Comparative Example 3 were observed by using an electron microscope (S-4800) manufactured by Hitachi Ltd. A case where the shape of the resist pattern after development had no pattern collapse and had good rectangularity was evaluated to be good and a case the shape had pattern collapse and did not have good rectangularity was evaluated to be poor. In the observation results, the minimum line width where there was no pattern collapse and rectangularity was good was defined as the resolution and used as an evaluation index. Furthermore, the minimum amount of electron beam energy, where a good pattern shape could be drawn, was defined as the sensitivity and used as an evaluation index. The results are shown in Table 2.

TABLE 2

| | Material for forming underlayer film | Resolution (nmL/S) | Sensitivity (μC/cm$^2$) | Resist pattern formation after development |
|---|---|---|---|---|
| Example 13 | Material described in Example 7 | 60 | 18 | Good |
| Comparative Example 3 | Not used | 90 | 38 | Poor |

As can be seen from Table 2, it was confirmed that the underlayer film of Example 7 was significantly excellent in resolution and sensitivity as compared with Comparative Example 3. It was also confirmed that the resist pattern shape after development had no pattern collapse and had good rectangularity. Furthermore, it was shown from the difference in the resist pattern shape after development that the material for forming an underlayer film for lithography in Example 7 had good adhesiveness with a resist material.

Example 14

Purification of BiF-1

To a four-neck flask (bottom outlet type) having a volume of 1000 mL was charged 150 g of a solution (10% by mass) in which BiF-1 obtained in Example 1 was dissolved in PGMEA, and heated to 80° C. with stirring. Then, 37.5 g of an aqueous oxalic acid solution (pH: 1.3) was added thereto, stirred for 5 minutes and thereafter left to stand for 30 minutes. The resultant was thus separated to an oil phase and an aqueous phase, and thus the aqueous phase was removed. Such an operation was repeated once, and thereafter the resulting oil phase was charged with 37.5 g of ultrapure water, stirred for 5 minutes and thereafter left to stand for 30 minutes to remove the aqueous phase. Such an operation was repeated three times, and thereafter the flask was subjected to pressure reduction to 200 hPa or less while being heated to 80° C., to thereby allow the remaining water content and PGMEA to be distilled off by concentration. Thereafter, dilution with PGMEA (EL grade, reagent produced by Kanto Chemical Co., Inc.) was made to adjust the concentration to 10% by mass, thereby providing a solution of BiF-1 having a reduced metal content, in PGMEA.

Reference Example 1

Purification Method with Ion Exchange Resin

After 25 g of an ion exchange resin (Mitsubishi Chemical Corporation, Diaion: SMT100-mixed resin) was swollen by cyclohexanone, the resultant was packed in a Teflon (registered trademark) column, and 500 mL of 1,3-dioxolane was allowed to flow through the column to thereby perform solvent displacement. Then, 500 g of a solution (10% by mass) of BiF-1 obtained in Example 1, dissolved in 1,3-dioxolane, was allowed to flow through the column to provide a solution of BiF-1 in dioxolane.

The contents of various metals were measured by ICP-MS with respect to the 10% by mass BiF-1 solution in PGMEA before treatment, and the solutions obtained in Example 14 and Reference Example 1. The measurement results are shown in Table 3.

TABLE 3

| | Metal content (ppb) | | | | | |
|---|---|---|---|---|---|---|
| | Na | Mg | K | Fe | Cu | Zn |
| Before treatment BiF-1 | >99 | 23.2 | >99 | >99 | 2.7 | 13.6 |
| Example 14 | 2.3 | 1.1 | 0.6 | 2.1 | 0.3 | 0.4 |
| Reference Example 1 | 0.3 | 0.5 | 1.0 | >99 | 1.2 | 0.4 |

The present application claims a priority based on Japanese Patent Application (Japanese Patent Application No. 2014-050768) filed on Mar. 13, 2014, the content of which is herein incorporated as reference.

INDUSTRIAL APPLICABILITY

The compound and the resin of the present invention have a relatively high carbon concentration, a relatively low oxygen concentration, a relatively high heat resistance and also a relatively high solvent solubility, and which can be applied to a wet process. Therefore, a material for forming an underlayer film for lithography and an underlayer film, using the compound or the resin of the present invention, can be widely and effectively utilized in various applications in which these properties are required. Therefore, the present invention can be widely and effectively utilized for, for example, an electric insulating material; a resist resin; a sealing resin for a semiconductor; an adhesive for a printed wiring board; an electric laminated board mounted on electrical equipment, electronic equipment, industrial equipment and the like; a matrix resin for a prepreg mounted on electrical equipment, electronic equipment, industrial equipment and the like; a material for a build-up laminated board; a resin for fiber-reinforced plastics; a sealing resin for a liquid crystal display panel; a paint; various coating agents; an adhesive; a coating agent for a semiconductor; a resist resin for a semiconductor; and a resin for forming an underlayer film. In particular, the present invention can be particularly effectively utilized in the field of an underlayer film for lithography and an underlayer film for a multilayer resist.

The invention claimed is:

1. A compound represented by the following formula (1):

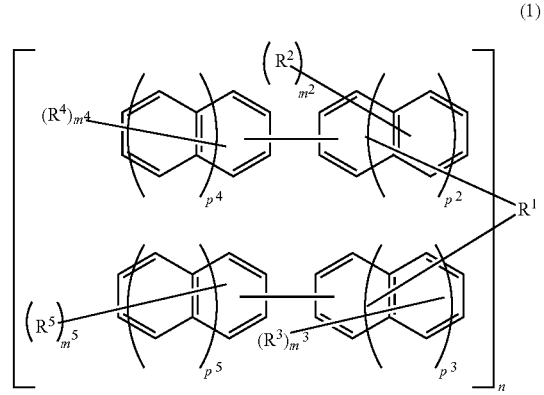

wherein $R^1$ includes 1-30 carbon atoms and is a group represented by $R^A$-$R^B$ where $R^A$ is a methine group and $R^B$ is an aryl group having 7 or more carbon atoms, each of $R^2$ to $R^5$ is independently a linear, branched or cyclic alkyl group having 1 to 10 carbon atoms, an aryl group having 6 to 10 carbon atoms, an alkenyl group having 2 to 10 carbon atoms, a thiol group or a hydroxyl group, wherein at least one $R^4$ and/or at least one $R^5$ is a hydroxyl group and/or a thiol group, each of $m^2$ and $m^3$ is independently an integer of 0 to 8, each of $m^4$ and $m^5$ is independently an integer of 0 to 9, wherein at least one of $m^4$ and $m^5$ is an integer of 1 to 9, n is an integer of 1, and each of $p^2$ to $p^5$ is independently an integer of 0 to 2.

2. The compound according to claim 1, wherein at least one $R^2$ and/or at least one $R^3$ is a hydroxyl group and/or a thiol group.

3. The compound according to claim 1, wherein the compound represented by the formula (1) is a compound represented by the following formula (1a):

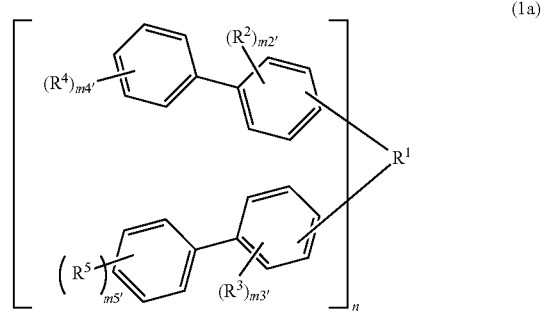

wherein $R^1$ to $R^5$ and n are the same as defined in the formula (1), each of $m^{2'}$ and $m^{3'}$ is independently an integer of 0 to 4, and each of $m^{4'}$ and $m^{5'}$ is independently an integer of 0 to 5, wherein at least one of $m^{4'}$ and $m^{5'}$ is an integer of 1 to 5.

4. The compound according to claim 3, wherein the compound represented by the formula (1a) is a compound represented by the following formula (1b):

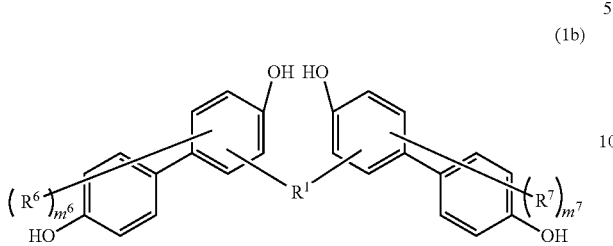

(1b)

wherein R¹ is the same as defined in the formula (1), each of $R^6$ and $R^7$ is independently a linear, branched or cyclic alkyl group having 1 to 10 carbon atoms, an aryl group having 6 to 10 carbon atoms, an alkenyl group having 2 to 10 carbon atoms, a thiol group or a hydroxyl group, and each of $m^6$ and $m^7$ is independently an integer of 0 to 7.

5. The compound according to claim 4, wherein the compound represented by the formula (1b) is represented by the following formula (BiF-1)

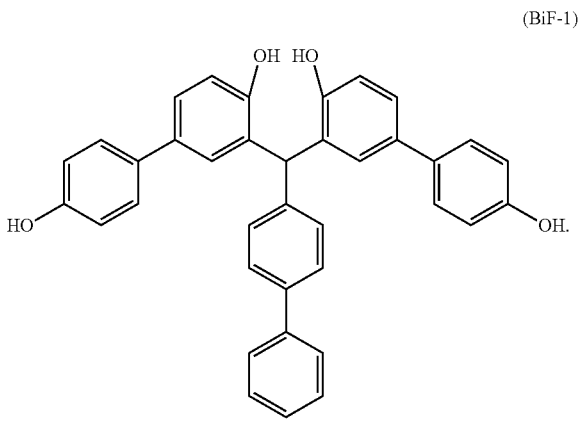 [SMILES: Oc1ccc(-c2ccc(O)c(C(c3ccc(-c4ccccc4)cc3)c3cc(-c4ccc(O)cc4)ccc3O)c2)cc1]

(BiF-1)

6. A resin obtained by using the compound according to claim 1 as a monomer.

7. A material for forming an underlayer film for lithography, comprising the compound according to claim 1.

8. The material for forming the underlayer film for lithography according to claim 7, further comprising an organic solvent.

9. The material for forming the underlayer film for lithography according to claim 7, further comprising an acid generator.

10. The material for forming the underlayer film for lithography according to claim 7, further comprising a crosslinking agent.

11. An underlayer film for lithography, formed from the material for forming the underlayer film for lithography according to claim 7.

12. A resist pattern forming method, comprising
step (A-1) of forming an underlayer film on a substrate by using the material for forming the underlayer film according to claim 7,
step (A-2) of forming at least one photoresist layer on the underlayer film, and
step (A-3) of, after step (A-2), irradiating a predetermined region of the photoresist layer with radiation, followed by developing with an alkali.

13. A circuit pattern forming method comprising
step (B-1) of forming an underlayer film on a substrate by using the material for forming the underlayer film according to claim 7,
step (B-2) of forming an intermediate layer film on the underlayer film by using a silicon atom-containing resist intermediate layer film material,
step (B-3) of forming at least one photoresist layer on the intermediate layer film,
step (B-4) of, after step (B-3), irradiating a predetermined region of the photoresist layer with radiation, followed by developing with an alkali to form a resist pattern, and
step (B-5) of, after step (B-4), etching the intermediate layer film with the resist pattern as a mask, etching the underlayer film with an obtained intermediate layer film pattern as an etching mask and etching the substrate with an obtained underlayer film pattern as an etching mask, to form a pattern on the substrate.

14. A method for purifying the compound according to claim 1, the method comprising
a step of bringing a solution comprising an organic solvent optionally immiscible with water, and the compound into contact with an acidic aqueous solution for extraction.

15. The method according to claim 14, wherein the acidic aqueous solution is an aqueous solution of at least one mineral acid selected from the group consisting of hydrochloric acid, sulfuric acid, nitric acid and phosphoric acid, or an aqueous solution of at least one organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid.

16. The method according to claim 14, wherein the organic solvent optionally immiscible with water is toluene, 2-heptanone, cyclohexanone, cyclopentanone, methyl isobutyl ketone, propylene glycol monomethyl ether acetate or ethyl acetate.

17. The method according to claim 14, further comprising a step of performing an extraction treatment with water, after the step of bringing the solution into contact with the acidic aqueous solution for extraction.

18. A resin having, as a repeating structure, the following structure represented by formula (2):

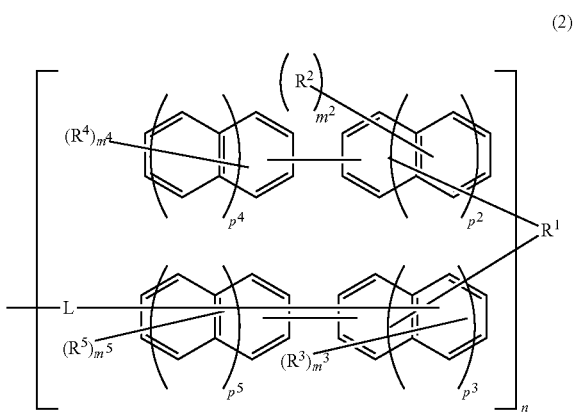

(2)

wherein $R^1$ is a 2n-valent group having 1 to 30 carbon atoms, each of $R^2$ to $R^5$ is independently a linear, branched or cyclic alkyl group having 1 to 10 carbon atoms, an aryl group having 6 to 10 carbon atoms, an alkenyl group having 2 to 10 carbon atoms, a thiol group or a hydroxyl group, wherein at least one $R^4$ and/or at least one $R^5$ is a hydroxyl group and/or a thiol group, L is a single bond, or a linear or branched alkylene group having 1 to 20 carbon atoms, each of $m^2$ and $m^3$ is independently an integer of 0 to 8, each of $m^4$ and $m^5$ is independently an integer of 0 to 9, wherein at least one of $m^4$ and $m^5$ is an integer of 1 to 9, n is an integer of 1 to 4, and each of $p^2$ to $p^5$ is independently an integer of 0 to 2.

19. A material for forming an underlayer film for lithography, comprising the resin according to claim 18.

20. The material for forming the underlayer film for lithography according to claim 19, further comprising an organic solvent.

21. The material for forming the underlayer film for lithography according to claim 19, further comprising an acid generator.

22. The material for forming the underlayer film for lithography according to claim 19, further comprising a crosslinking agent.

23. An underlayer film for lithography, formed from the material for forming the underlayer film for lithography according to claim 19.

24. A resist pattern forming method, comprising
step (A-1) of forming an underlayer film on a substrate by using the material for forming the underlayer film according to claim 19,
step (A-2) of forming at least one photoresist layer on the underlayer film, and
step (A-3) of, after step (A-2), irradiating a predetermined region of the photoresist layer with radiation, followed by developing with an alkali.

25. A circuit pattern forming method comprising
step (B-1) of forming an underlayer film on a substrate by using the material for forming the underlayer film according to claim 19,
step (B-2) of forming an intermediate layer film on the underlayer film by using a silicon atom-containing resist intermediate layer film material,
step (B-3) of forming at least one photoresist layer on the intermediate layer film,
step (B-4) of, after step (B-3), irradiating a predetermined region of the photoresist layer with radiation, followed by developing with an alkali to form a resist pattern, and
step (B-5) of, after step (B-4), etching the intermediate layer film with the resist pattern as a mask, etching the underlayer film with an obtained intermediate layer film pattern as an etching mask and etching the substrate with an obtained underlayer film pattern as an etching mask, to form a pattern on the substrate.

* * * * *

UNITED STATES PATENT AND TRADEMARK OFFICE
CERTIFICATE OF CORRECTION

PATENT NO. : 10,294,183 B2  
APPLICATION NO. : 15/125503  
DATED : May 21, 2019  
INVENTOR(S) : Takashi Makinoshima and Masatoshi Echigo Page 1 of 1

It is certified that error appears in the above-identified patent and that said Letters Patent is hereby corrected as shown below:

In the Claims

Column 68, Line (40):
In Claim 1, delete "is an integer of" and insert -- is --, therefor.

Column 69, Line (6-14):

In Claim 4, delete " 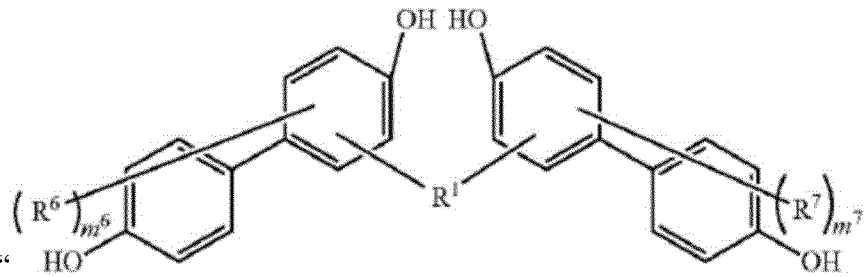 " and insert -- 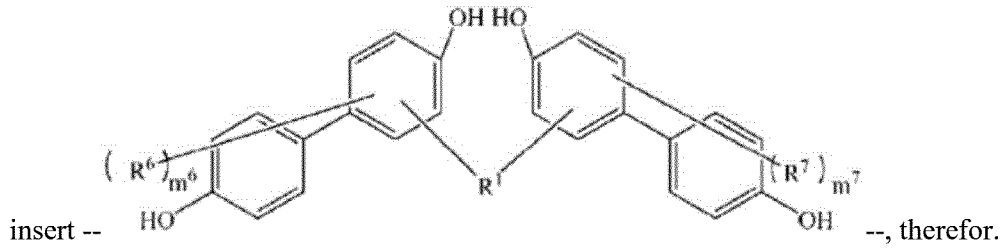 --, therefor.

Signed and Sealed this  
Fifteenth Day of October, 2019

Andrei Iancu  
*Director of the United States Patent and Trademark Office*